(12) United States Patent
Mann et al.

(10) Patent No.: US 8,906,825 B2
(45) Date of Patent: Dec. 9, 2014

(54) HERBICIDAL COMPOSITIONS COMPRISING 4-AMINO-3-CHLORO-5-FLUORO-6-(4-CHLORO-2-FLUORO-3-METHOXYPHENYL) PYRIDINE-2-CARBOXYLIC ACID OR A DERIVATIVE THEREOF AND TRIAZOLOPYRIMIDINE SULFONAMIDES

(71) Applicant: Dow AgroSciences LLC, Indianapolis, IN (US)

(72) Inventors: Richard K. Mann, Franklin, IN (US); Carla N. Yerkes, Crawfordsville, IN (US); Norbert M. Satchivi, Carmel, IN (US); Monte R. Weimer, Pittsboro, IN (US); Nelson M. Carranza Garzon, Ibague (CO)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 13/832,978

(22) Filed: Mar. 15, 2013

(65) Prior Publication Data
US 2014/0031229 A1   Jan. 30, 2014

Related U.S. Application Data

(60) Provisional application No. 61/675,037, filed on Jul. 24, 2012.

(51) Int. Cl.
| | | |
|---|---|---|
| *A01N 25/26* | (2006.01) | |
| *A01N 43/46* | (2006.01) | |
| *A01N 43/40* | (2006.01) | |
| *A01N 43/653* | (2006.01) | |

(52) U.S. Cl.
CPC .............. *A01N 43/40* (2013.01); *A01N 43/653* (2013.01)
USPC .......................................... 504/100; 504/134

(58) Field of Classification Search
CPC ................................ A01N 43/40; A01N 43/90
See application file for complete search history.

(56) References Cited

U.S. PATENT DOCUMENTS

| | | | |
|---|---|---|---|
| 7,314,849 B2 | 1/2008 | Balko et al. | |
| 7,622,641 B2 | 11/2009 | McCutchen et al. | |
| 2009/0062121 A1 | 3/2009 | Satchivi et al. | |
| 2010/0137137 A1 | 6/2010 | Rosinger et al. | |
| 2011/0082162 A1 | 4/2011 | Lorsbach et al. | |
| 2011/0207607 A1 | 8/2011 | Satchivi et al. | |
| 2012/0115727 A1 | 5/2012 | Satchivi et al. | |
| 2012/0190551 A1 | 7/2012 | Yerkes et al. | |
| 2013/0109569 A1 | 5/2013 | Dave et al. | |
| 2013/0310256 A1 | 11/2013 | Yerkes et al. | |
| 2014/0031210 A1 | 1/2014 | Yerkes et al. | |
| 2014/0031211 A1 | 1/2014 | Yerkes et al. | |
| 2014/0031212 A1 | 1/2014 | Yerkes et al. | |
| 2014/0031213 A1 | 1/2014 | Yerkes et al. | |
| 2014/0031214 A1 | 1/2014 | Yerkes et al. | |
| 2014/0031215 A1 | 1/2014 | Yerkes et al. | |
| 2014/0031216 A1 | 1/2014 | Yerkes et al. | |
| 2014/0031217 A1 | 1/2014 | Yerkes et al. | |
| 2014/0031218 A1 | 1/2014 | Mann et al. | |
| 2014/0031219 A1 | 1/2014 | Yerkes et al. | |
| 2014/0031220 A1 | 1/2014 | Yerkes et al. | |
| 2014/0031221 A1 | 1/2014 | Yerkes et al. | |
| 2014/0031222 A1 | 1/2014 | Yerkes et al. | |
| 2014/0031227 A1 | 1/2014 | Yerkes et al. | |
| 2014/0031228 A1 | 1/2014 | Mann et al. | |

FOREIGN PATENT DOCUMENTS

WO    WO 2007/082098    7/2007

OTHER PUBLICATIONS

Thomas, S., Written Opinion of the International Search Authority for PCT/US2013/051289, Dec. 3, 2013, pp. 1-5, ISA/US.
Thomas, S., International Search Report for PCT/US2013/051289, Dec. 3, 2013, pp. 1-4, ISA/US.
Synthesis of Esters: Esterification Reactions, obtained via google. com in U.S. Appl. No. 13/840,306, obtained online Mar. 8, 2014.
Chui, M.P., Non-Final Office Action in U.S. Appl. No. 13/840,306, Mar. 13, 2014, pp. 1-12, USPTO.
Pryor, A.N., Notice of Allowance and Fee(s) Due for U.S. Appl. No. 13/834,706, Mar. 12, 2014, pp. 1-13, USPTO.
Pryor, A.N., Notice of Allowance and Fee(s) Due for U.S. Appl. No. 13/833,315, May 12, 2014, pp. 1-8, USPTO.

(Continued)

*Primary Examiner* — Alton Pryor
(74) *Attorney, Agent, or Firm* — Michael R. Asam; Faegre Baker Daniels LLP.

(57) ABSTRACT

Provided herein are synergistic herbicidal compositions containing (a) a compound of formula (I):

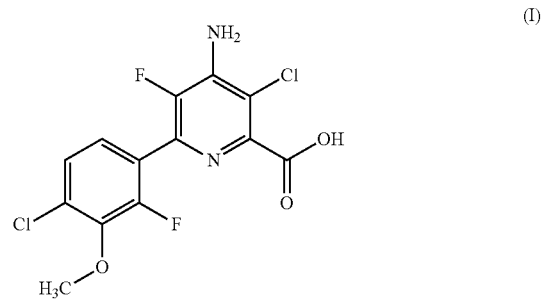

or an agriculturally acceptable salt or ester thereof and (b) triazolopyrimidine sulfonamides, including, but not limited to, cloransulam-methyl, diclosulam, florasulam, flumetsulam, metosulam, penoxsulam, and pyroxsulam. The compositions provide control of undesirable vegetation, e.g., in direct-seeded, water-seeded and transplanted rice, cereals, wheat, barley, oats, rye, sorghum, corn/maize, sugarcane, sunflower, oilseed rape, canola, sugar beet, soybean, cotton, pineapple, pastures, grasslands, rangelands, fallowland, turf, tree and vine orchards, aquatics, plantation crops, vegetables, industrial vegetation management (IVM) and rights of way (ROW).

18 Claims, No Drawings

(56) References Cited

OTHER PUBLICATIONS

Pryor, A.N., Notice of Allowance and Fee(s) Due for U.S. Appl. No. 13/833,315, Mar. 20, 2014, pp. 1-11, USPTO.
Pryor, A.N., Notice of Allowance and Fee(s) Due for U.S. Appl. No. 13/833,362, May 29, 2014, pp. 1-8, USPTO.
Pryor, A.N., Notice of Allowance and Fee(s) Due for U.S. Appl. No. 13/833,372, May 14, 2014, pp. 1-8, USPTO.
Pryor, A.N., Notice of Allowance and Fee(s) Due for U.S. Appl. No. 13/833,659, Mar. 17, 2014, pp. 1-12, USPTO.
Pryor, A.N., Notice of Allowance and Fee(s) Due for U.S. Appl. No. 13/833,923, May 2, 2014, pp. 1-9, USPTO.
Pryor, A.N., Notice of Allowance and Fee(s) Due for U.S. Appl. No. 13/833,965, Apr. 1, 2014, pp. 1-8, USPTO.
Pryor, A.N., Notice of Allowance and Fee(s) Due for U.S. Appl. No. 13/834,326, May 13, 2014, pp. 1-4, USPTO.
Pryor, A.N., Notice of Allowance and Fee(s) Due for U.S. Appl. No. 13/834,326, Apr. 2, 2014, pp. 1-9, USPTO.
Pryor, A.N., Notice of Allowance and Fee(s) Due for U.S. Appl. No. 13/836,653, Apr. 2, 2014, pp. 1-8, USPTO.
Pryor, A.N., Notice of Allowance and Fee(s) Due for U.S. Appl. No. 13/836,653, Jun. 17, 2014, pp. 1-5, USPTO.
Pryor, A.N., Notice of Allowance and Fee(s) Due for U.S. Appl. No. 13/837,990, Apr. 1, 2014, pp. 1-8, USPTO.
Pryor, A.N., Notice of Allowance and Fee(s) Due for U.S. Appl. No. 13/839,043, May 27, 2014, pp. 1-5, USPTO.
Pryor, A.N., Notice of Allowance and Fee(s) Due for U.S. Appl. No. 13/839,043, Mar. 24, 2014, pp. 1-8, USPTO.
Pryor, A.N., Notice of Allowance and Fee(s) Due for U.S. Appl. No. 13/840,236, Apr. 25, 2014, pp. 1-8, USPTO.
Pryor, A.N., Notice of Allowance and Fee(s) Due for U.S. Appl. No. 13/840,303, Apr. 25, 2014, pp. 1-8, USPTO.
Pryor, A.N., Notice of Allowance and Fee(s) Due for U.S. Appl. No. 13/840,346, Jun. 4, 2014, pp. 1-8, USPTO.
Pryor, A.N., Notice of Allowance and Fee(s) Due for U.S. Appl. No. 13/840,419, May 5, 2014, pp. 1-8, USPTO.
Pryor, A.N., Notice of Allowance and Fee(s) Due for U.S. Appl. No. 13/840,488, May 2, 2014, pp. 1-8, USPTO.

HERBICIDAL COMPOSITIONS COMPRISING 4-AMINO-3-CHLORO-5-FLUORO-6-(4-CHLORO-2-FLUORO-3-METHOXYPHENYL)PYRIDINE-2-CARBOXYLIC ACID OR A DERIVATIVE THEREOF AND TRIAZOLOPYRIMIDINE SULFONAMIDES

PRIORITY CLAIM

This application claims the benefit of U.S. provisional patent application No. 61/675,037 filed on Jul. 24, 2012, this provisional application is incorporated herein by reference in its entirety.

FIELD

Provided herein are herbicidal compositions comprising (a) 4-amino-3-chloro-5-fluoro-6-(4-chloro-2-fluoro-3-methoxyphenyl)pyridine-2-carboxylic acid or an agriculturally acceptable ester or salt thereof and (b) triazolopyrimidine sulfonamides.

Provided herein are also methods of controlling undesirable vegetation comprising applying (a) 4-amino-3-chloro-5-fluoro-6-(4-chloro-2-fluoro-3-methoxyphenyl)pyridine-2-carboxylic acid or an agriculturally acceptable ester or salt thereof and (b) triazolopyrimidine sulfonamides.

BACKGROUND

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use. However, there remains a need for compositions and methods that are effective in controlling undesirable vegetation.

SUMMARY

A first embodiment of the invention provided herein includes herbicidal compositions comprising an herbicidally effective amount of (a) a compound of the formula (I)

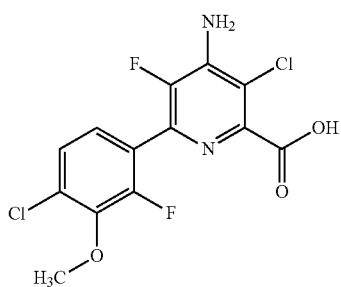

(I)

or an agriculturally acceptable salt or ester thereof, and (b) at least one triazolopyrimidine sulfonamide.

A second embodiment includes the mixture of the first embodiment in which formula (I) is present in at least one of the following forms: a carboxylic acid, a carboxylate salt, an aralkyl, an alkyl ester, an unsubstituted benzyl, a substituted benzyl, a $C_{1-4}$ alkyl, and/or an n-butyl ester.

A third embodiment includes the mixture according to the first or second embodiments wherein the triazolopyrimidine sulfonamide (b) is at least one compound selected from the group consisting of: cloransulam-methyl, diclosulam, florasulam, flumetsulam, metosulam, penoxsulam, or pyroxsulam or an agriculturally acceptable salt, carboxylic acid, carboxylate salt, or ester thereof of at least one of the aforementioned triazolopyrimidine sulfonamides.

A fourth embodiment includes the mixtures according to the first, second, or third embodiments in which the triazolopyrimidine sulfonamide in the mixture is cloransulam-methyl wherein the weight ratio of the compound of formula (I) to cloransulam-methyl given in units of gae/ha to gai/ha or gae/ha to gae/ha is selected from the group of ranges of ratios and ratios consisting of: from about 1:31 to about 137:1, about 1:1, about 2:1, about 4:1, about 2:1, about 2.5:1, about 1:1, about 0.5:1, about 10:1, about 20:1, about 2.4:1, about 4.8:1, about 1:1.17, about 1:1.2, about 2.4:1, about 1:17, about 1:1.1, about 1.0:0.55, about 1.0:1.1, about 1.8:1, about 1.2:1, about 0.15:1, about 0.3:1, about 1:2.2, about 1.0:4.4, from about 1:20 to about 1:100, from about 1:10 to about 1:50, from about 1:5 to about 1:25, from about 1:8 to about 15:1 and from about 2:1 to about 1:1.

A fifth embodiment includes the mixtures according to the first, second, or third embodiments in which the triazolopyrimidine sulfonamide in the mixture is penoxsulam wherein the weight ratio of the compound of formula (I) to penoxsulam given in units of gae/ha to gai/ha or gae/ha to gae/ha is selected from the group of ranges of ratios and ratios consisting of: from about 1:23 to about 65:1, about 1:1, about 2:1, about 1:4, about 2:1 to about 1:4; about 1:2 to about 2:1, about 1:2 to about 4:1, about 1:1 to about 4:1, about 1:2.5 to about 1:0.65, about 1:1.5, about 1:0.75; about 1:0.38, about 2.6:1, about 1:4 to about 1:2, about 1:4 to about 1:1, 1.2:1 to about 10:1, about 5:1, about 2.4:1, about 4.8:1, about 17:1, about 11:1, about 4.3:1, about 3; 1, about 2.2:1, about 2.7:1, about 0.6:1, about 0.4:1, about 0.7:1, about 1.0:1.25, about 1.0:1.7, about 3:1, about 4:1, about 9.6:1, from about 1:20 to 1:60, from about 1:15 to 50:1, from about 1:2 to 40:1, from about 1:10 to 30:1, from about 1:8 to 20:1, from about 1:7 to 15:1, from about 1:6 to about 10:1, from about 1:5 to 8:1, from about 1:4 to 6; 1, from about 1:3 to 5:1, from about 1:2 to about 4:1, from about 1:1 to about 3:1, from about 1:11 to about 1:46 and from about 1:1 to about 5:1.

A sixth embodiment includes the mixtures according to the first, second, or third embodiments in which the triazolopyrimidine sulfonamide in the mixture is diclosulam wherein the weight ratio of the compound of formula (I) to diclosulam given in units of gae/ha to gai/ha or gae/ha to gae/ha is selected from the group of ranges of ratios and ratios consisting of: about 1:26 to about 26:1, about 1:0.38, about 1:0.75, about 1:0.38, about 1.3:1, about 0.7:1, about 2.6:1, about 0.7:1 to about 1.3:1, about 1.5:1, from about 1:25 to 25:1, from about 1:20 to 20:1, from about 1:15 to 15:1, from about 1:10 to 10:1, from 1:5 to about 5:1, from 1:4 to about 4:1, from about 1:3 to about 3:1, and about 1.3:1 to about 0.6:1.

A seventh embodiment includes the mixtures according to the first, second, or third embodiments in which the triazolopyrimidine sulfonamide in the mixture is flumetsulam wherein the weight ratio of the compound of formula (I) to flumetsulam given in units of gae/ha to gai/ha or gae/ha to gae/ha is selected from the group of ranges of ratios and ratios consisting of: from 1:40 to about 272:1, about 1.25:1, about 2.5:1, about 5:1, about 1.5:1, about 0.32:1, about 6.4:1, from about 1:35 to 270:1, from about 1:30 to 250:1, from about 1:20 to 150:1, from about 1:15 to 100:1, from 1:10 to 75:1, from about 1:9 to about 70:1, from about 1:8 to about 60:1, from about 1:7 to 50:1, from about 1:6 to 40:1, from about 1:5 to 30:1, from about 1:4 to 20:1, from about 1:3 to 15:1, from about 1:2 to 10:1, from about 1:3 to about 5:1 and from about 1.28:1 to about 1.5:1.

A eighth embodiment includes the mixtures according to the first, second, or third embodiments in which the triazolopyrimidine sulfonamide in the mixture is metosulam wherein the weight ratio of the compound of formula (I) to metosulam given in units of gae/ha to gai/ha or gae/ha to gae/ha is selected from the group of ranges of ratios and ratios consisting of: from about 1:5 to about 300:1, about 1:0.8, about 1:0.4, about 1.5:1, from about 1:4 to 200:1, from about 1:3 to 100:1, from about 1:2 to about 50:1 and about 1.28 to about 5.1:1.

A ninth embodiment includes the mixtures according to the first, second, or third embodiments in which the triazolopyrimidine sulfonamide in the mixture is florasulam wherein the weight ratio of the compound of formula (I) to florasulam given in units of gae/ha to gai/ha or gae/ha to gae/ha is selected from the group of ranges of ratios and ratios consisting of: from about 1:5 to about 300:1, about 1.0:0.75, about 7.0:1.0, about 4:1, about 2:3, about 2.1, about 1:1, about 1:2, about 1:4, about 7:1, from about 1:4 to 200:1, from about 1:3 to about 100:1, from about 1:25 to about 50:1, from about 1:2 to about 30:1, from about 1:1 to about 25:1, from about 1.35:1 to about 7:1 and from about 4:1 to about 2.3:1.

A tenth embodiment includes the mixtures according to the first, second, or third embodiments in which the triazolopyrimidine sulfonamide in the mixture is pyroxsulam wherein the weight ratio of the compound of formula (I) to pyroxsulam given in units of gae/ha to gai/ha or gae/ha to gae/ha is selected from the group of ranges of ratios and ratios consisting of: from about 1:11 to about 75:1, about 1:1, about 2:1, about 2.3:1, about 4:1, about 8:1, about 11:1, about 1.0:0.4, about 1:10 to about 1:70, from about 1:9 to about 1:60, from about 1:8 to about 1:50, from about 1:7 to about 1:40, from about 1:6 to about 1:30, from about 1:5 to about 1:25, from about 1:4 to about 1:20, from about 1:3 to about 1:15, from about 1:2 to about 1:10, from about 1:1 to about 1:8 and about 2.33:1.

An eleventh embodiment includes any composition according to the first through the tenth embodiments wherein the mixture further comprises at least one an agriculturally acceptable agent selected from the group consisting of an adjuvant, a carrier, or a safener.

A twelfth embodiment includes methods of controlling undesirable vegetation comprising the step of applying or otherwise contacting vegetation and/or soil, and/or water with a herbicidally effective amount of at least one mixture according to the first through the eleventh embodiments.

A thirteenth embodiment includes methods according to the twelfth embodiment wherein undesirable vegetation is controlled according to at least technique selected from the group consisting of: direct-seeded, water-seeded, and/or transplanted rice, cereals, wheat, barley, oats, rye, sorghum, corn/maize, sugarcane, sunflower, oilseed rape, canola, sugar beet, soybean, cotton, pineapple, pastures, grasslands, rangelands, fallowland, turf, tree and vine orchards, aquatics, plantation crops, vegetables, industrial vegetation management (IVM), or rights-of-way (ROW).

A fourteenth embodiment includes methods according to the twelfth and/or thirteenth embodiments wherein a herbicidally effective amount of the mixture is applied either pre- or post emergently to at least one of the following: a crop, a field, a ROW, or a rice paddy.

A fifteenth embodiment includes methods according to the eleventh through the fourteenth embodiments wherein the undesirable vegetation may be controlled by practicing at least one of the methods in plants that are resistant or tolerant of agents that act by at least one mode selected from the groups consisting of: in glyphosate-, 5-enolpyruvylshikimate-3-phosphate (EPSP) synthase inhibitor-, glufosinate-, glutamine synthetase inhibitor-, dicamba-, phenoxy auxin-, pyridyloxy auxin-, synthetic auxin-, auxin transport inhibitor-, aryloxyphenoxypropionate-, cyclohexanedione-, phenylpyrazoline-, acetyl CoA carboxylase (ACCase) inhibitor-, imidazolinone-, sulfonylurea-, pyrimidinylthiobenzoate-, triazolopyrimidine-, sulfonylaminocarbonyltriazolinone-, acetolactate synthase (ALS) or acetohydroxy acid synthase (AHAS) inhibitor-, 4-hydroxyphenyl-pyruvate dioxygenase (HPPD) inhibitor-, phytoene desaturase inhibitor-, carotenoid biosynthesis inhibitor-, protoporphyrinogen oxidase (PPO) inhibitor-, cellulose biosynthesis inhibitor-, mitosis inhibitor-, microtubule inhibitor-, very long chain fatty acid inhibitor-, fatty acid and lipid biosynthesis inhibitor-, photosystem I inhibitor-, photosystem II inhibitor-, protoporphyrinogen oxidase (PPO) inhibitor-, triazine-, or bromoxynil A sixteenth embodiment includes a at least one method according to the eleventh through the fifteenth embodiments wherein a plant that is resistant or tolerant to at least one herbicide is treated, and where the resistant or tolerant crop possesses multiple or stacked traits conferring tolerance to multiple herbicides or inhibitors of multiple herbicide modes of action, in some embodiments the treated plant that expresses resistance to a herbicide is a itself undesirable vegetation.

A seventeenth embodiment includes methods according to the sixteen embodiment, wherein the resistant or tolerant weed is a biotype with resistance or tolerance to multiple herbicides, multiple chemical classes, inhibitors of multiple herbicide modes-of-action, or via multiple resistance mechanisms.

An eighteenth embodiment includes at least one of the methods according to the sixteenth or seventeenth embodiments, wherein the resistant or tolerant undesirable plant is a biotype resistant or tolerant to at least one agent and/or an agent that acts through at least one mode selected from the group one or more modes of action consisting of: acetolactate synthase (ALS) inhibitors or acetohydroxy acid synthase (AHAS), photosystem II inhibitors, acetyl CoA carboxylase (ACCase) inhibitors, synthetic auxins, auxin transport inhibitors, photosystem I inhibitors, 5-enolpyruvylshikimate-3-phosphate (EPSP) synthase inhibitors, microtubule assembly inhibitors, fatty acid and lipid synthesis inhibitors, protoporphyrinogen oxidase (PPO) inhibitors, carotenoid biosynthesis inhibitors, very long chain fatty acid (VLCFA) inhibitors, phytoene desaturase (PDS) inhibitors, glutamine synthetase inhibitors, 4-hydroxyphenyl-pyruvate-dioxygenase (HPPD) inhibitors, mitosis inhibitors, cellulose biosynthesis inhibitors, herbicides with multiple modes-of-action, quinclorac, arylaminopropionic acids, difenzoquat, endothall, or organoarsenicals.

A nineteenth embodiment includes methods of controlling undesirable vegetation comprising the step of applying a herbicidally effective amount of at least one mixture according to the fifth embodiment wherein the amount of the mixture is applied at a rate, expressed in gai/ha or gae/ha of penoxsulam selected from the group of rates and ranges of rates consisting of, about: 2, 4.28, 4.8, 8.75, 17, 35, 50 and 100.

A twentieth embodiment includes methods according to the fifth and nineteenth embodiments wherein the controlled plant is at least one plant selected from the group consisting of: IPOHE, LEFCH, LEFPA, BRAPP, ECHCG, SCPMA, CYPDI, CYPES and ISCRU, still other embodiments include controlling plants from the genera consisting of: *Ipohe, Leptochloa, Brachiaria, Echinochloa, Scirpus, Cyperus* and *Ischaemum.*

A twenty-first embodiment includes methods of controlling undesirable vegetation comprising the step of applying a herbicidally effective amount of at least one a mixture according to the sixth embodiment wherein the amount of the mixture is applied at a rate, expressed in gai/ha or gae/ha of disclosulam selected from the group of rates and ranges of rates consisting of, about: 2, 6.62, 13.25, and 26.5.

A twenty-second embodiment includes methods according to the sixth and twenty-first embodiments wherein the controlled plant is at least one plant selected from the group consisting of: LEFCH, CYPRO, and ECHCG, still other embodiments include controlling plants from the genera consisting of: *Leptochloa, Cyperus,* and *Echinochloa.*

A twenty-third embodiment includes methods of controlling undesirable vegetation comprising the step of applying a herbicidally effective amount of at least one a mixture according to the seventh embodiment wherein the amount of the mixture is applied at a rate, expressed in gai/ha or gae/ha of flumetsulam selected from the group of rates and ranges of rates consisting of, about: 2, 6.25, 12.5, 25, and 50.

A twenty-fourth embodiment includes methods according to the seventh and twenty-third embodiments wherein the controlled plant is at least one plant selected from the group consisting of: BRARP and CYPIR, still other embodiments include controlling plants from the genera consisting of: Brachiaria and *Cyperus.*

A twenty-fifth embodiment includes methods of controlling undesirable vegetation comprising the step of applying a herbicidally effective amount of at least one a mixture according to the eighth embodiment wherein the amount of the mixture is applied at a rate, expressed in gai/ha or gae/ha of metosulam selected from the group of rates and ranges of rates consisting of, about: 2, 6.25, 12.5, and 25.

A twenty-sixth embodiment includes methods according to the eighth and twenty-fifth embodiments wherein the controlled plant is at least one plant selected from the group consisting of, LEFCH, still other embodiments include controlling plants from the genus *Leptochloa.*

A twenty-seventh embodiment includes methods of controlling undesirable vegetation comprising the step of applying a herbicidally effective amount of at least one a mixture according to the ninth embodiment wherein the amount of the mixture is applied at a rate, expressed in gai/ha or gae/ha of florasulam selected from the group of rates and ranges of rates consisting of, about: 2, 1.25, 3.75, 6.65, 12.5, 25, and 50.

A twenty-eighth embodiment includes methods according to the ninth and twenty-seventh embodiments wherein the controlled plant is at least one plant selected from the group consisting of: SASKR, VEPRE, VIOTR, MATCH, CIRAR, and LAMPU, still other embodiments include controlling plants from the genera consisting of: *Salsola, Veronica, Viola, Chamomilla, Cirscum,* and *Lamium.*

A twenty-ninth embodiment includes methods of controlling undesirable vegetation comprising the step of applying a herbicidally effective amount of at least one a mixture according to the tenth embodiment wherein the amount of the mixture is applied at a rate, expressed in gai/ha or gae/ha of pyroxsulam selected from the group of rates and ranges of rates consisting of, about: 2, 3.75, 7.5, and 50.

A thirtieth embodiment includes methods according to the tenth and twenty-ninth embodiments wherein the controlled plant is at least one plant selected from the group consisting of: CIRAR, still other embodiments include controlling plants from the genus *Cirsium.*

A thirty-first embodiment includes methods of controlling undesirable vegetation comprising the step of applying a herbicidally effective amount of at least one a mixture according to the fourth embodiment wherein the amount of the mixture is applied at a rate, expressed in gai/ha or gae/ha of cloransulam-methyl selected from the group of rates and ranges of rates consisting of, about: 1, 2, 2.19, 4.38, 8.75, 17.5, 35, and 70.

A thirty-second embodiment includes methods according to the fourth and thirty-first embodiments wherein the controlled plant is at least one plant selected from the group consisting of: DIGSA, LEFCH, CYPIR, ECHCG, CYPDI, and FIMMI, still other embodiments include controlling plants from the genera consisting of: *Digitaria, Leptochloa, Cyperus, Echinochloa,* and *Fimbristylis.*

Provided herein are also methods of controlling undesirable vegetation comprising applying (a) a compound of formula (I) or an agriculturally acceptable ester or salt thereof and (b) triazolopyrimidine sulfonamides.

Exemplary triazolopyrimidine sulfonamides include, but are not limited to, cloransulam-methyl, diclosulam, florasulam, flumetsulam, metosulam, penoxsulam, and pyroxsulam or an agriculturally acceptable salt, carboxylic acid, carboxylate salt, or ester thereof.

Provided herein are herbicidal compositions comprising a herbicidally effective amount of (a) a compound of the formula (I)

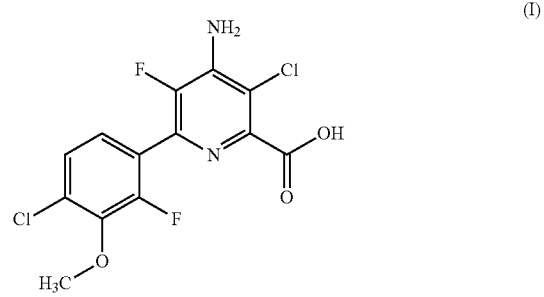 [SMILES: COc1c(Cl)ccc(-c2nc(C(=O)O)c(Cl)c(N)c2F)c1F]

(I)

or an agriculturally acceptable salt or ester of thereof, and (b) triazolopyrimidine sulfonamides. The compositions may also contain an agriculturally acceptable adjuvant or carrier.

Provided herein are also methods of controlling undesirable vegetation comprising applying (a) a compound of formula (I) or an agriculturally acceptable ester or salt thereof and (b) triazolopyrimidine sulfonamides or an agriculturally acceptable salt or ester thereof.

DETAILED DESCRIPTION

Definitions

As used herein, the compound of formula (I) has the following structure:

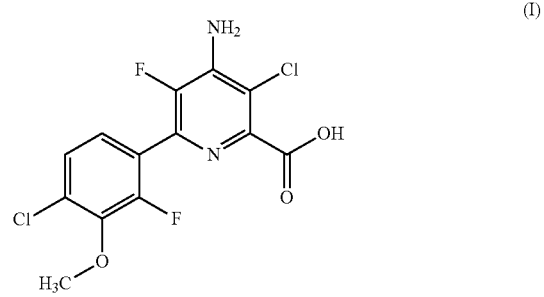 [SMILES: COc1c(Cl)ccc(-c2nc(C(=O)O)c(Cl)c(N)c2F)c1F]

(I)

The compound of formula (I) can be identified by the name 4-amino-3-chloro-6-(4-chloro-2-fluoro-3-methoxyphenyl)-5-fluoropyridine-2-carboxylic acid and has been described in U.S. Pat. No. 7,314,849 (B2), which is incorporated herein by reference in its entirety. Exemplary uses of the compound of the formula (I) include controlling undesirable vegetation, including grass, broadleaf and sedge weeds, in multiple non-crop and cropping situations.

As used herein, triazolopyrimidine sulfonamides are a chemical class of herbicides having a triazolopyrimidine sulfonamide core structure. Without being limited to any theory, their mode of action is believed to involve the inhibition of acetolactate synthase (ALS), an enzyme common to plants and microorganisms but not found in animals. Exemplary herbicidal uses of triazolopyrimidine sulfonamides include, but are not limited to, use for control of nuisance sedge, broadleaf and grass weeds.

Exemplary triazolopyrimidine sulfonamides include, but are not limited to, cloransulam-methyl, diclosulam, florasulam, flumetsulam, metosulam, penoxsulam, and pyroxsulam.

As used herein, cloransulam-methyl is methyl 3-chloro-2-[[(5-ethoxy-7-fluoro[1,2,4]triazolo[1,5-c]pyrimidin-2-yl)sulfonyl]amino]benzoate and possesses the following structure:

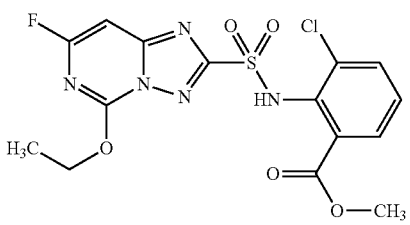 [SMILES: CCOc1nc(F)cc2nc(S(=O)(=O)Nc3c(Cl)cccc3C(=O)OC)nn12]

Its herbicidal activity is exemplified in Tomlin, C., ed. A World Compendium The Pesticide Manual. 15$^{th}$ ed. Alton: BCPC Publications, 2009 (hereafter "*The Pesticide Manual*, Fifteenth Edition, 2009."). Exemplary uses of cloransulam-methyl include its use as a herbicide for post-emergence control of broadleaf weeds in soybeans and other broadleaf crops.

As used herein, diclosulam is N-(2,6-dichlorophenyl)-5-ethoxy-7-fluoro[1,2,4]triazolo[1,5-c]pyrimidine-2-sulfonamide and possesses the following structure:

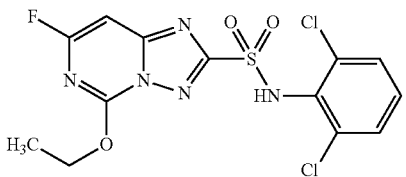 [SMILES: CCOc1nc(F)cc2nc(S(=O)(=O)Nc3c(Cl)cccc3Cl)nn12]

Its herbicidal activity is exemplified in *The Pesticide Manual*, Fifteenth Edition, 2009. Exemplary uses of diclosulam include its use as a herbicide for broadleaf weed control in peanuts and soybeans.

As used herein, florasulam is N-(2,6-difluorophenyl)-8-fluoro-5-methoxy[1,2,4]triazolo[1,5-c]pyrimidine-2-sulfonamide and possesses the following structure:

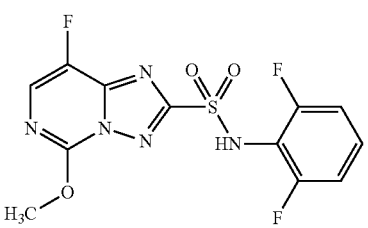 [SMILES: COc1ncc(F)c2nc(S(=O)(=O)Nc3c(F)cccc3F)nn12]

Its herbicidal activity is exemplified in *The Pesticide Manual*, Fifteenth Edition, 2009. Exemplary uses of florasulam includes its use as a herbicide in post-emergence control of broadleaf weeds in cereals and maize.

As used herein, flumetsulam is N-(2,6-difluorophenyl)-5-methyl[1,2,4]triazolo[1,5-a]pyrimidine-2-sulfonamide and possesses the following structure:

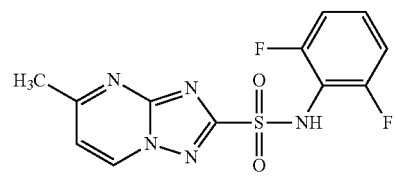 [SMILES: Cc1ccn2nc(S(=O)(=O)Nc3c(F)cccc3F)nc2n1]

Its herbicidal activity is exemplified in *The Pesticide Manual*, Fifteenth Edition, 2009. Exemplary uses of flumetsulam include its use as a herbicide for the control of broadleaf weeds and grasses in soya beans, field peas and maize.

As used herein, metosulam is N-(2,6-dichloro-3-methylphenyl)-5,7-dimethoxy[1,2,4]triazolo[1,5-a]pyrimidine-2-sulfonamide and possesses the following structure:

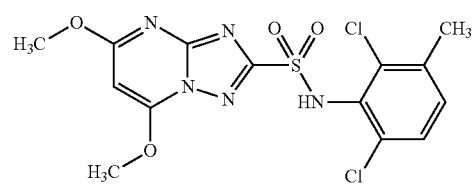

Its herbicidal activity is exemplified in *The Pesticide Manual*, Fifteenth Edition, 2009. Exemplary uses of metosulam includes its use as a herbicide for post-emergence control of broadleaf weeds in wheat, barley and rye, and pre- or post-emergence control of broadleaf weeds in maize.

As used herein, penoxsulam is 2-(2,2-difluoroethoxy)-N-(5,8-dimethoxy[1,2,4]triazolo[1,5-c]pyrimidin-2-yl)-6-(trifluoromethyl)benzenesulfonamide and possesses the following structure:

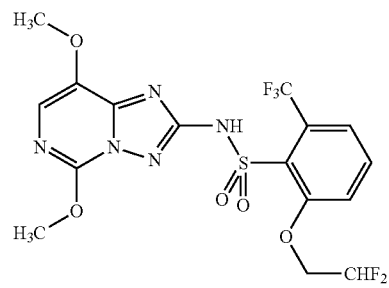 [SMILES: COc1cnc(OC)n2nc(NS(=O)(=O)c3c(OCC(F)F)cccc3C(F)(F)F)nc12]

Its herbicidal activity is exemplified in *The Pesticide Manual*, Fifteenth Edition, 2009. Exemplary uses of penoxsulam includes its use as a herbicide for post-emergence control of *Echinochloa* spp., broadleaf weeds and annual sedge weeds in rice, as well as *Echinochloa* spp. and broadleaf weeds in sorghum, turf, cereals and tree and vine crops. In another example, penoxsulam is used to control aquatic weeds in lakes and ponds.

As used herein, pyroxsulam is N-(5,7-dimethoxy[1,2,4] triazolo[1,5-a]pyrimidin-2-yl)-2-methoxy-4-(trifluoromethyl)-3-pyridinesulfonamide and possesses the following structure:

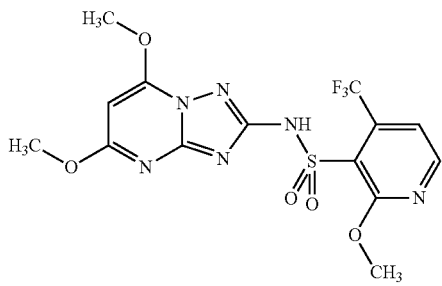 [SMILES: COc1cc(OC)n2nc(NS(=O)(=O)c3c(C(F)(F)F)ccnc3OC)nc2n1]

Its herbicidal activity is exemplified in *The Pesticide Manual*, Fifteenth Edition, 2009. Exemplary uses of pyroxsulam includes its use as a herbicide for broad spectrum post-emergence control of annual grass and broadleaf weeds in cereals.

As used herein, herbicide means a compound, e.g., active ingredient that kills, controls or otherwise adversely modifies the growth of plants.

As used herein, a herbicidally effective or vegetation controlling amount is an amount of active ingredient which causes an adversely modifying effect to the vegetation e.g., causing deviations from natural development, killing, effecting regulation, causing desiccation, causing retardation, and the like.

As used herein, controlling undesirable vegetation means preventing, reducing, killing, or otherwise adversely modifying the development of plants and vegetation. Described herein are methods of controlling undesirable vegetation through the application of certain herbicide combinations or compositions. Methods of application include, but are not limited to applications to the vegetation or locus thereof, e.g., application to the area adjacent to the vegetation, as well as pre-emergence, post-emergence, foliar (broadcast, directed, banded, spot, mechanical, over-the-top, or rescue), and in-water applications (emerged and submerged vegetation, broadcast, spot, mechanical, water-injected, granular broadcast, granular spot, shaker bottle or stream spray) via hand, backpack, machine, tractor, or aerial (airplane and helicopter) application methods.

As used herein, plants and vegetation include, but are not limited to, germinant seeds, emerging seedlings, plants emerging from vegetative propagules, immature vegetation, and established vegetation.

As used herein, agriculturally acceptable salts and esters refer to salts and esters that exhibit herbicidal activity, or that are or can be converted in plants, water, or soil to the referenced herbicide. Exemplary agriculturally acceptable esters are those that are or can be hydrolyzed, oxidized, metabolized, or otherwise converted, e.g., in plants, water, or soil, to the corresponding carboxylic acid which, depending on the pH, may be in the dissociated or undissociated form.

Exemplary salts include those derived from alkali or alkaline earth metals and those derived from ammonia and amines. Exemplary cations include sodium, potassium, magnesium, and aminium cations of the formula:

$$R^1R^2R^3R^4N^+$$

wherein $R^1$, $R^2$, $R^3$ and $R^4$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R^1$, $R^2$, $R^3$ and $R^4$ are sterically compatible. Additionally, any two of $R^1$, $R^2$, $R^3$ and $R^4$ together may represent an aliphatic difunctional moiety containing one to twelve carbon atoms and up to two oxygen or sulfur atoms. Salts can be prepared by treatment with a metal hydroxide, such as sodium hydroxide, with an amine, such as ammonia, trimethylamine, diethanolamine, 2-methylthiopropylamine, bisallylamine, 2-butoxyethylamine, morpholine, cyclododecylamine, or benzylamine or with a tetraalkylammonium hydroxide, such as tetramethylammonium hydroxide or choline hydroxide.

Exemplary esters include those derived from $C_1$-$C_{12}$ alkyl, $C_3$-$C_{12}$ alkenyl, $C_3$-$C_{12}$ alkynyl or $C_7$-$C_{10}$ aryl-substituted alkyl alcohols, such as methyl alcohol, isopropyl alcohol, 1-butanol, 2-ethylhexanol, butoxyethanol, methoxypropanol, allyl alcohol, propargyl alcohol, cyclohexanol or unsubstituted or substituted benzyl alcohols. Benzyl alcohols may be substituted with from 1-3 substituents independently selected from halogen, $C_1$-$C_4$ alkyl or $C_1$-$C_4$ alkoxy. Esters can be prepared by coupling of the acids with the alcohol using any number of suitable activating agents such as those used for peptide couplings such as dicyclohexylcarbodiimide (DCC) or carbonyl diimidazole (CDI); by reacting the acids with alkylating agents such as alkylhalides or alkylsulfonates in the presence of a base such as triethylamine or lithium carbonate; by reacting the corresponding acid chloride of an acid with an appropriate alcohol; by reacting the corresponding acid with an appropriate alcohol in the presence of an acid catalyst or by transesterification.

Compositions and Methods

Provided herein are herbicidal compositions comprising an herbicidally effective amount of (a) a compound of the formula (I)

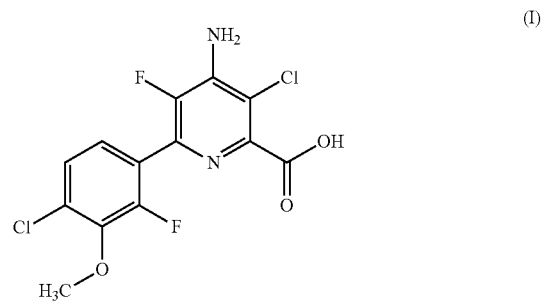 [SMILES: COc1c(Cl)ccc(-c2nc(C(=O)O)c(Cl)c(N)c2F)c1F]

or an agriculturally acceptable salt or ester of thereof, and (b) triazolopyrimidine sulfonamides. Exemplary triazolopyrimidine sulfonamides include, but are not limited to, cloransulam-methyl, diclosulam, florasulam, flumetsulam, metosulam, penoxsulam, and pyroxsulam or an agriculturally acceptable salt, carboxylic acid, carboxylate salt, or ester thereof.

Provided herein are also methods of controlling undesirable vegetation comprising contacting the vegetation or the locus thereof, i.e., area adjacent to the vegetation, with or applying to the soil or water to prevent the emergence or growth of vegetation a herbicidally effective amount of the compound of formula (I) or agriculturally acceptable salt or ester thereof and (b) triazolopyrimidine sulfonamides. In certain embodiments, the methods employ the compositions described herein.

Furthermore, in some embodiments, the combination of compound (I) or an agriculturally acceptable salt or ester thereof and triazolopyrimidine sulfonamides, or an agriculturally acceptable salt or ester thereof exhibits synergism, e.g., the herbicidal active ingredients are more effective in combination than when applied individually. Synergism has been defined as "an interaction of two or more factors such that the effect when combined is greater than the predicted effect based on the response of each factor applied separately." Senseman, S., ed. Herbicide Handbook. $9^{th}$ ed. Lawrence: Weed Science Society of America, 2007. In certain embodiments, the compositions exhibit synergy as determined by the Colby's equation. Colby, S. R. 1967. Calculation of the synergistic and antagonistic response of herbicide combinations. Weeds 15:20-22.

In some embodiments, the compound of formula (I) or salt or ester thereof and cloransulam-methyl, diclosulam, florasulam, flumetsulam, metosulam, penoxsulam, and pyroxsulam or an agriculturally acceptable salt, carboxylic acid, carboxylate salt, or ester thereof, are formulated in one composition, tank mixed, applied simultaneously, or applied sequentially.

Herbicidal activity is exhibited by the compounds when they are applied directly to the plant or to the locus of the plant at any stage of growth. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted to promote non-selective or selective herbicidal action. In some embodiments, the compositions described herein are applied as a post-emergence application, pre-emergence application, or in-water application to flooded paddy rice or water bodies (e.g., ponds, lakes and streams), to relatively immature undesirable vegetation to achieve the maximum control of weeds.

In some embodiments, the compositions and methods provided herein are utilized to control weeds in crops, including but not limited to direct-seeded, water-seeded and transplanted rice, cereals, wheat, barley, oats, rye, sorghum, corn/maize, sugarcane, sunflower, oilseed rape, canola, sugar beet, soybean, cotton, pineapple, pastures, grasslands, rangelands, fallowland, turf, tree and vine orchards, plantation crops, vegetables, aquatics, industrial vegetation management (IVM) and rights-of-way (ROW).

In certain embodiments, the compositions and methods provided herein are utilized to control weeds in rice. In certain embodiments, the rice is direct seeded, water seeded, or transplanted rice.

The compositions and methods described herein may be used to control undesirable vegetation in glyphosate-tolerant-, 5-enolpyruvylshikimate-3-phosphate (EPSP) synthase inhibitor-tolerant-, glufosinate-tolerant-, glutamine synthetase inhibitor-tolerant-, dicamba-tolerant-, phenoxy auxin-tolerant-, pyridyloxy auxin-tolerant-, auxin-tolerant-, auxin transport inhibitor-tolerant-, aryloxyphenoxypropionate-tolerant-, cyclohexanedione-tolerant-, phenylpyrazoline-tolerant-, acetyl CoA carboxylase (ACCase) inhibitor-tolerant-, imidazolinone-tolerant-, sulfonylurea-tolerant-, pyrimidinylthiobenzoate-tolerant-, dimethoxy-pyrimidine-tolerant, triazolopyrimidine-tolerant-, sulfonylaminocarbonyltriazolinone-tolerant-, acetolactate synthase (ALS) or acetohydroxy acid synthase (AHAS) inhibitor-tolerant-, 4-hydroxyphenyl-pyruvate dioxygenase (HPPD) inhibitor-tolerant-, phytoene desaturase inhibitor-tolerant-, carotenoid biosynthesis inhibitor-tolerant-, protoporphyrinogen oxidase (PPO) inhibitor-tolerant-, cellulose biosynthesis inhibitor-tolerant-, mitosis inhibitor-tolerant-, microtubule inhibitor-tolerant-, very long chain fatty acid inhibitor-tolerant-, fatty acid and lipid biosynthesis inhibitor-tolerant-, photosystem I inhibitor-tolerant-, photosystem II inhibitor-tolerant-, triazine-tolerant-, and bromoxynil-tolerant-crops (such as, but not limited to, soybean, cotton, canola/oilseed rape, rice, cereals, corn, sorghum, sunflower, sugar beet, sugarcane, turf, etc.), for example, in conjunction with glyphosate, EPSP synthase inhibitors, glufosinate, glutamine synthase inhibitors, dicamba, phenoxy auxins, pyridyloxy auxins, synthetic auxins, auxin transport inhibitors, aryloxyphenoxypropionates, cyclohexanediones, phenylpyrazolines, ACCase inhibitors, imidazolinones, sulfonylureas, pyrimidinylthiobenzoates, dimethoxy-pyrimidines, triazolopyrimidines, sulfonylaminocarbonyltriazolinones, ALS or AHAS inhibitors, HPPD inhibitors, phytoene desaturase inhibitors, carotenoid biosynthesis inhibitors, PPO inhibitors, cellulose biosynthesis inhibitors, mitosis inhibitors, microtubule inhibitors, very long chain fatty acid inhibitors, fatty acid and lipid biosynthesis inhibitors, photosystem I inhibitors, photosystem II inhibitors, triazines, and bromoxynil The compositions and methods may be used in controlling undesirable vegetation in crops possessing multiple or stacked traits conferring tolerance to multiple chemistries and/or inhibitors of multiple modes of action. In some embodiments, the compound of formula (I) or salt or ester thereof and complementary herbicide or salt or ester thereof are used in combination with herbicides that are selective for the crop being treated and which complement the spectrum of weeds controlled by these compounds at the application rate employed. In some embodiments, the compositions described herein and other complementary herbicides are applied at the same time, either as a combination formulation, a tank mix or sequentially.

The compositions and methods may be used in controlling undesirable vegetation in crops possessing agronomic stress tolerance (including but not limited to drought, cold, heat, salt, water, nutrient, fertility, pH), pest tolerance (including but not limited to insects, fungi and pathogens) and crop improvement traits (including but not limited to yield; protein, carbohydrate, or oil content; protein, carbohydrate, or oil composition; plant stature and plant architecture).

The compositions and methods provided herein are utilized to control undesirable vegetation. Undesirable vegetation includes, but is not limited to, undesirable vegetation that occurs in rice, cereals, wheat, barley, oats, rye, sorghum, corn/maize, sugarcane, sunflower, oilseed rape, canola, sugar beet, soybean, cotton, pineapple, pastures, grasslands, rangelands, fallowland, turf, tree and vine orchards, aquatics, plantation crops, vegetables, industrial vegetation management (IVM) and rights-of-way (ROW).

In some embodiments, the methods provided herein are utilized to control undesirable vegetation in rice. In certain embodiments, the undesirable vegetation is *Brachiaria platyphylla* (Groseb.) Nash or *Urochloa platyphylla* (Nash) R.D. Webster (broadleaf signalgrass, BRAPP), *Digitaria sanguinalis* (L.) Scop. (large crabgrass, DIGSA), *Echinochloa* species (ECHSS), *Echinochloa crus-galli* (L.) P. Beauv. (barnyardgrass, ECHCG), *Echinochloa crus-pavonis* (Kunth) Schuh. (gulf cockspur, ECHCV), *Echinochloa colonum* (L.) LINK (junglerice, ECHCO), *Echinochloa oryzoides* (Ard.) Fritsch (early watergrass, ECHOR), *Echi-* nochloa oryzicola (Vasinger) Vasinger (late watergrass, ECHPH), *Echinochloa phyllopogon* (Stapf) Koso-Pol. (rice barnyardgrass, ECHPH), *Echinochloa polystachya* (Kunth) Hitchc. (creeping river grass, ECHPO), *Ischaemum rugosum* Salisb. (saramollagrass, ISCRU), *Leptochloa chinensis* (L.) Nees (Chinese sprangletop, LEFCH), *Leptochloa fascicularis* (Lam.) Gray (bearded sprangletop, LEFFA), *Leptochloa panicoides* (Presl.) Hitchc. (Amazon sprangletop, LEFPA), *Oryza* species (red and weedy rice, ORYSS), *Panicum dichotomiflorum* (L.) Michx. (fall panicum, PANDI), *Paspalum dilatatum* Poir. (dallisgrass, PASDI), *Rottboellia cochinchinensis* (Lour.) W.D. Clayton (itchgrass, ROOEX), *Cyperus* species (CYPSS), *Cyperus difformis* L. (smallflower flatsedge, CYPDI), *Cyperus dubius* Rottb. (MAPDU), *Cyperus esculentus* L. (yellow nutsedge, CYPES), *Cyperus iria* L. (rice flatsedge, CYPIR), *Cyperus rotundus* L. (purple nutsedge, CYPRO), *Cyperus serotinus* Rottb./C.B. Clarke (tidalmarsh flatsedge, CYPSE), *Eleocharis* species (ELOSS), *Fimbristylis miliacea* (L.) Vahl (globe fringerush, FIMMI), *Schoenoplectus* species (SCPSS), *Schoenoplectus juncoides* Roxb. (Japanese bulrush, SCPJU), *Bolboschoenus maritimus* (L.) Palla or *Schoenoplectus maritimus* L. Lye (sea clubrush, SCPMA), *Schoenoplectus mucronatus* L. (ricefield bulrush, SCPMU), *Aeschynomene* species, (jointvetch, AESSS), *Alternanthera philoxeroides* (Mart.) Griseb. (alligatorweed, ALRPH), *Alisma plantago-aquatica* L. (common waterplantain, ALSPA), *Amaranthus* species, (pigweeds and amaranths, AMASS), *Ammannia coccinea* Rottb. (redstem, AMMCO), *Commelina benghalensis* L. (Benghal dayflower, COMBE), *Eclipta alba* (L.) Hassk. (American false daisy, ECLAL), *Heteranthera limosa* (SW.) Willd./Vahl (ducksalad, HETLI), *Heteranthera reniformis* R. & P. (roundleaf mudplantain, HETRE), *Ipomoea* species (morningglories, IPOSS), *Ipomoea hederacea* (L.) Jacq. (ivyleaf morningglory, IPOHE), *Lindernia dubia* (L.) Pennell (low false pimpernel, LIDDU), *Ludwigia* species (LUDSS), *Ludwigia linifolia* Poir. (southeastern primrose-willow, LUDLI), *Ludwigia octovalvis* (Jacq.) Raven (longfruited primrose-willow, LUDOC), *Monochoria korsakowii* Regel & Maack (monochoria, MOOKA), *Monochoria vaginalis* (Berm. F.) C. Presl ex Kuhth, (monochoria, MOOVA), *Murdannia nudiflora* (L.) Brenan (doveweed, MUDNU), *Polygonum pensylvanicum* L., (Pennsylvania smartweed, POLPY), *Polygonum persicaria* L. (ladysthumb, POLPE), *Polygonum hydropiperoides* Michx. (POLHP, mild smartweed), *Rotala indica* (Willd.) Koehne (Indian toothcup, ROTIN), *Sagittaria* species, (arrowhead, SAGSS), *Sesbania exaltata* (Raf.) Cory/Rydb. Ex Hill (hemp sesbania, SEBEX), or *Sphenoclea zeylanica* Gaertn. (gooseweed, SPDZE).

In some embodiments, the methods provided herein are utilized to control undesirable vegetation in cereals. In certain embodiments, the undesirable vegetation is *Alopecurus myosuroides* Huds. (blackgrass, ALOMY), *Apera spica-venti* (L.) Beauv. (windgrass, APESV), *Avena fatua* L. (wild oat, AVEFA), *Bromus tectorum* L. (downy brome, BROTE), *Lolium multiflorum* Lam. (Italian ryegrass, LOLMU), *Phalaris minor* Retz. (littleseed canarygrass, PHAMI), *Poa annua* L. (annual bluegrass, POANN), *Setaria pumila* (Poir.) Roemer & J.A. Schultes (yellow foxtail, SETLU), *Setaria viridis* (L.) Beauv. (green foxtail, SETVI), *Amaranthus retroflexus* L. (redroot pigweed, AMARE), *Brassica* species (BRSSS), *Chenopodium album* L. (common lambsquarters, CHEAL), *Cirsium arvense* (L.) Scop. (Canada thistle, CIRAR), *Galium aparine* L. (catchweed bedstraw, GALAP), *Kochia scoparia* (L.) Schrad. (*kochia*, KCHSC), *Lamium purpureum* L. (purple deadnettle, LAMPU), *Matricaria recutita* L. (wild chamomile, MATCH), *Matricaria matricarioides* (Less.) Porter (pineappleweed, MATMT), *Papaver rhoeas* L. (common poppy, PAPRH), *Polygonum convolvulus* L. (wild buckwheat, POLCO), *Salsola tragus* L. (Russian thistle, SASKR), *Sinapis* species (SINSS), *Sinapis arvensis* L. (wild mustard, SINAR), *Stellaria media* (L.) Vill. (common chickweed, STEME), *Veronica persica* Poir. (Persian speedwell, VERPE), *Viola arvensis* Murr. (field violet, VIOAR), or *Viola tricolor* L. (wild violet, VIOTR).

In some embodiments, the methods provided herein are utilized to control undesirable vegetation in range and pasture, fallowland, IVM and ROW. In certain embodiments, the undesirable vegetation is *Ambrosia artemisiifolia* L. (common ragweed, AMBEL), *Cassia obtusifolia* (sickle pod, CASOB), *Centaurea maculosa* auct. non Lam. (spotted knapweed, CENMA), *Cirsium arvense* (L.) Scop. (Canada thistle, CIRAR), *Convolvulus arvensis* L. (field bindweed, CONAR), *Daucus carota* L. (wild carrot, DAUCA), *Euphorbia esula* L. (leafy spurge, EPHES), *Lactuca serriola* L./Torn. (prickly lettuce, LACSE), *Plantago lanceolata* L. (buckhorn plantain, PLALA), *Rumex obtusifolius* L. (broadleaf dock, RUMOB), *Sida spinosa* L. (prickly sida, SIDSP), *Sinapis arvensis* L. (wild mustard, SINAR), *Sonchus arvensis* L. (perennial sowthistle, SONAR), *Solidago* species (goldenrod, SOOSS), *Taraxacum officinale* G. H. Weber ex Wiggers (dandelion, TAROF), *Trifolium repens* L. (white clover, TRFRE), or *Urtica dioica* L. (common nettle, URTDI).

In some embodiments, the methods provided herein are utilized to control undesirable vegetation found in row crops, tree and vine crops, and perennial crops. In certain embodiments, the undesirable vegetation is *Alopecurus myosuroides* Huds. (blackgrass, ALOMY), *Avena fatua* L. (wild oat, AVEFA), *Brachiaria decumbens* Stapf. or *Urochloa decumbens* (Stapf) R.D. Webster (Surinam grass, BRADC), *Brachiaria brizantha* (Hochst. ex A. Rich.) Stapf. or *Urochloa brizantha* (Hochst. ex A. Rich.) R.D. (beard grass, BRABR), *Brachiaria platyphylla* (Groseb.) Nash or *Urochloa platyphylla* (Nash) R.D. Webster (broadleaf signalgrass, BRAPP), *Brachiaria plantaginea* (Link) Hitchc. or *Urochloa plantaginea* (Link) R.D. Webster (alexandergrass, BRAPL), *Cenchrus echinatus* L. (southern sandbar, CENEC), *Digitaria horizontalis* Willd. (Jamaican crabgrass, DIGHO), *Digitaria insularis* (L.) Mez ex Ekman (sourgrass, TRCIN), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) Link (junglerice, ECHCO), *Eleusine indica* (L.) Gaertn. (goosegrass, ELEIN), *Lolium multiflorum* Lam. (Italian ryegrass, LOLMU), *Panicum dichotomiflorum* Michx. (fall panicum, PANDI), *Panicum miliaceum* L. (wild-proso millet, PANMI), *Setaria faberi* Herrm. (giant foxtail, SETFA), *Setaria viridis* (L.) Beauv. (green foxtail, SETVI), *Sorghum halepense* (L.) Pers. (Johnsongrass, SORHA), *Sorghum bicolor* (L.) Moench ssp. *Arundinaceum* (shattercane, SORVU), *Cyperus esculentus* L. (yellow nutsedge, CYPES), *Cyperus rotundus* L. (purple nutsedge, CYPRO), *Abutilon theophrasti* Medik. (velvetleaf, ABUTH), *Amaranthus* species (pigweeds and amaranths, AMASS), *Ambrosia artemisiifolia* L. (common ragweed, AMBEL), *Ambrosia psilostachya* DC. (western ragweed, AMBPS), *Ambrosia trifida* L. (giant ragweed, AMBTR), *Anoda cristata* (L.) Schlecht. (spurred anoda, ANVCR), *Asclepias syriaca* L. (common milkweed, ASCSY), *Bidens pilosa* L. (hairy beggarticks, BIDPI), *Borreria* species (BOISS), *Borreria alata* (Aubl.) DC. or *Spermacoce alata* Aubl. (broadleaf buttonweed, BOILF), *Spermacose latifolia* (broadleaved button weed, BOILF), *Chenopodium album* L. (common lambsquarters, CHEAL), *Cirsium arvense* (L.) Scop. (Canada thistle, CIRAR), *Commelina benghalensis* L. (tropical spiderwort, COMBE), *Datura stramonium* L. (jimsonweed, DATST), *Daucus carota* L. (wild carrot, DAUCA), *Euphorbia heterophylla* L. (wild poinsettia, EPHHL), *Euphorbia hirta* L. or *Chamaesyce hirta* (L.) Millsp. (garden spurge, EPHHI), *Euphorbia dentata* Michx. (toothed spurge, EPHDE), *Erigeron bonariensis* L. or *Conyza bonariensis* (L.) Cronq. (hairy fleabane, ERIBO), *Erigeron canadensis* L. or *Conyza canadensis* (L.) Cronq. (Canadian fleabane, ERICA), *Conyza sumatrensis* (Retz.) E.H. Walker (tall fleabane, ERIFL), *Helianthus annuus* L. (common sunflower, HELAN), *Jacquemontia tamnifolia* (L.) Griseb. (smallflower morningglory, IAQTA), *Ipomoea hederacea* (L.) Jacq. (ivyleaf morningglory, IPOHE), *Ipomoea lacunosa* L. (white morningglory, IPOLA), *Lactuca serriola* L./Torn. (prickly lettuce, LACSE), *Portulaca oleracea* L. (common purslane, POROL), *Richardia* species (pusley, RCHSS), *Sida* species (sida, SIDSS), *Sida spinosa* L. (prickly *sida*, SIDSP), *Sinapis arvensis* L. (wild mustard, SINAR), *Solanum ptychanthum* Dunal (eastern black nightshade, SOLPT), *Tridax procumbens* L. (coat buttons, TRQPR), or *Xanthium strumarium* L. (common cocklebur, XANST).

In some embodiments, the methods provided herein are utilized to control undesirable vegetation in turf. In certain embodiments, the undesirable vegetation is *Bellis perennis* L. (English daisy, BELPE), *Cyperus esculentus* L. (yellow nutsedge, CYPES), *Cyperus* species (CYPSS), *Digitaria sanguinalis* (L.) Scop. (large crabgrass, DIGSA), *Diodia virginiana* L. (Virginia buttonweed, DIQVI), *Euphorbia* species (spurge, EPHSS), *Glechoma hederacea* L. (ground ivy, GLEHE), *Hydrocotyle umbellata* L. (dollarweed, HYDUM), *Kyllinga* species (*kyllinga*, KYLSS), *Lamium amplexicaule* L. (henbit, LAMAM), *Murdannia nudiflora* (L.) Brenan (doveweed, MUDNU), *Oxalis* species (woodsorrel, OXASS), *Plantago major* L. (broadleaf plantain, PLAMA), *Plantago lanceolata* L. (buckhorn/narrowleaf plantain, PLALA), *Phyllanthus urinaria* L. (chamberbitter, PYLTE), *Rumex obtusifolius* L. (broadleaf dock, RUMOB), *Stachys floridana* Shuttlew. (Florida betony, STAFL), *Stellaria media* (L.) Vill. (common chickweed, STEME), *Taraxacum officinale* G.H. Weber ex Wiggers (dandelion, TAROF), *Trifolium repens* L. (white clover, TRFRE), or *Viola* species (wild violet, VIOSS).

In some embodiments, the compositions and methods provided herein are utilized to control undesirable vegetation consisting of grass, broadleaf and sedge weeds. In certain embodiments, the compositions and methods provided herein are utilized to control undesirable vegetation including *Brachiaria, Chamomilla, Cirsium, Cyperus, Digitaria, Echinochloa, Fimbristylis, Ischaemum, Ipomoea, Lamium, Leptochloa, Matricaria, Salsola, Schoenoplectus, Veronica* and *Viola*.

In some embodiments, the combination of compound (I) or agriculturally acceptable ester or salt thereof and cloransulam-methyl, diclosulam, florasulam, metosulam, penoxsulam, and pyroxsulam or agriculturally acceptable salt or ester thereof are used to control *Brachiaria platyphylla* (Griseb.) Nash or *Urochloa platyphylla* (Nash) R.D. Webster (broadleaf signalgrass, BRAPP), *Chamomilla chamomilla* (L.) Rydb. (scented mayweed, MATCH), *Cyperus difformis* L. (smallflower umbrella sedge, CYPDI), *Cyperus esculentus* L. (yellow nutsedge, CYPES), *Cirsium arvense* (L.) Scop. (Canada thistle, CIRAR), *Cyperus iria* L. (rice flatsedge, CYPIR), *Digitaria sanguinalis* (L.) Scop. (large crabgrass, DIGSA), *Echinochloa crus-galli* (L.) Beauv. (barnyardgrass, ECHCG), *Echinochloa* spp (ECHSS), *Fimbristylis miliacea* (L.) Vahl (globe fringerush, FIMMI), *Ipomoea hederacea* Jacq. (ivyleaf morningglory, IPOHE), *Ischaemum rugosum* Salisb. (saramollagrass, ISCRU), *Lamium purpureum* (L.) (purple deadnettle, LAMPU), *Leptochloa chinensis* (L.) Nees (Chinese sprangletop, LEFCH), *Leptochloa panicoides* (J. Presl) A.S. Hitchc. (Amazon sprangletop, LEFPA), *Salsola iberica* (L.) (Russian thistle, SASKR), *Schoenoplectus juncoides* (Roxb.) Palla (Japanese bulrush, SCPJU), *Veronica persica* Poir. (bird's-eye speedwell, VERPE) and *Viola tricolor* (L.) (wild pansy, VIOTR).

The compounds of formula I or agriculturally acceptable salt or ester thereof may be used to control herbicide resistant or tolerant weeds. The methods employing the combination of a compound of formula I or agriculturally acceptable salt or ester thereof and the compositions described herein may also be employed to control herbicide resistant or tolerant weeds. Exemplary resistant or tolerant weeds include, but are not limited to, biotypes resistant or tolerant to acetolactate synthase (ALS) or acetohydroxy acid synthase (AHAS) inhibitors (e.g., imidazolinones, sulfonylureas, pyrimidinylthiobenzoates, triazolopyrimidines, sulfonylaminocarbonyltriazolinones), photosystem II inhibitors (e.g., phenylcarbamates, pyridazinones, triazines, triazinones, uracils, amides, ureas, benzothiadiazinones, nitriles, phenylpyridazines), acetyl CoA carboxylase (ACCase) inhibitors (e.g., aryloxyphenoxypropionates, cyclohexanediones, phenylpyrazolines), synthetic auxins (e.g., benzoic acids, phenoxycarboxylic acids, pyridine carboxylic acids, quinoline carboxylic acids), auxin transport inhibitors (e.g., phthalamates, semicarbazones), photosystem I inhibitors (e.g., bipyridyliums), 5-enolpyruvylshikimate-3-phosphate (EPSP) synthase inhibitors (e.g., glyphosate), glutamine synthetase inhibitors (e.g., glufosinate, bialafos), microtubule assembly inhibitors (e.g., benzamides, benzoic acids, dinitroanilines, phosphoramidates, pyridines), mitosis inhibitors (e.g., carbamates), very long chain fatty acid (VLCFA) inhibitors (e.g., acetamides, chloroacetamides, oxyacetamides, tetrazolinones), fatty acid and lipid synthesis inhibitors (e.g., phosphorodithioates, thiocarbamates, benzofuranes, chlorocarbonic acids), protoporphyrinogen oxidase (PPO) inhibitors (e.g., diphenylethers, N-phenylphthalimides, oxadiazoles, oxazolidinediones, phenylpyrazoles, pyrimidindiones, thiadiazoles, triazolinones), carotenoid biosynthesis inhibitors (e.g., clomazone, amitrole, aclonifen), phytoene desaturase (PDS) inhibitors (e.g., amides, anilidex, furanones, phenoxybutan-amides, pyridiazinones, pyridines), 4-hydroxyphenyl-pyruvate-dioxygenase (HPPD) inhibitors (e.g., callistemones, isoxazoles, pyrazoles, triketones), cellulose biosynthesis inhibitors (e.g., nitriles, benzamides, quinclorac, triazolocarboxamides), herbicides with multiple modes-of-action such as quinclorac, and unclassified herbicides such as arylaminopropionic acids, difenzoquat, endothall, and organoarsenicals. Exemplary resistant or tolerant weeds include, but are not limited to, biotypes with resistance or tolerance to multiple herbicides, biotypes with resistance or tolerance to multiple chemical classes, biotypes with resistance or tolerance to multiple herbicide modes-of-action, and biotypes with multiple resistance or tolerance mechanisms (e.g., target site resistance or metabolic resistance).

In certain embodiments of the compositions and methods described herein, the compound of formula (I) or salt or ester thereof is used in combination with cloransulam-methyl or salt, carboxylic acid, carboxylate salt, or ester thereof. With regard to the compositions, in some embodiments, the weight ratio of the compound of formula (I) or salt or ester thereof to cloransulam-methyl or salt, carboxylic acid, carboxylate salt, or ester thereof is within the range from about 1:31 to about 137:1. In certain embodiments, the weight ratio of the compound of formula (I) or salt or ester thereof to cloransulam-methyl or salt, carboxylic acid, carboxylate salt, or ester thereof is within the range from about 1:2 to about 10:1. In special embodiments, the weight ratio of the compound of formula (I) or salt or ester thereof to cloransulam-methyl or salt, carboxylic acid, carboxylate salt, or ester thereof is within the range from about 1:8 to about 15:1. In certain embodiments, the weight ratio of the compound of formula (I) or salt or ester thereof to cloransulam-methyl or salt, carboxylic acid, carboxylate salt, or ester thereof is within the range from about 1:4 to about 22:1. In certain embodiments, the weight ratio of the compound of formula (I) or salt or ester thereof to cloransulam-methyl or salt, carboxylic acid, carboxylate salt, or ester thereof is within the range from about 1:2 to about 11:1. In certain embodiments, the compositions provided herein comprise the compound of formula (I) or its benzyl ester and cloransulam-methyl. In one embodiment, the composition comprises the compound of formula (I) and cloransulam-methyl, wherein the weight ratio of the compound of formula (I) to cloransulam-methyl is from about 1:1.7 to about 11:1. In one embodiment, the composition comprises the benzyl ester of the compound of formula (I) and cloransulam-methyl, wherein the weight ratio of the benzyl ester of the compound of formula (I) to cloransulam-methyl is from about 1:2 to about 4:1. In one embodiment, the composition comprises the benzyl ester of the compound of formula (I) and cloransulam-methyl, wherein the weight ratio of the benzyl ester of the compound of formula (I) to cloransulam-methyl is from about 1:2 to about 4:1. In a special embodiment, the composition comprises the benzyl ester of the compound of formula (I) and cloransulam-methyl, wherein the weight ratio of the benzyl ester of the compound of formula (I) to cloransulam-methyl is from about 1:8 to about 15:1. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate from about 4 grams active ingredient per hectare (gai/ha) to about 362 gai/ha based on the total amount of active ingredients in the composition. In certain embodiments, the composition is applied at an application rate from about 6 gai/ha to about 40 gai/ha based on the total amount of active ingredients in the composition. In special embodiments, the composition is applied at an application rate from about 6 gai/ha to about 67 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and cloransulam-methyl or salt, carboxylic acid, carboxylate salt, or ester thereof, e.g., sequentially or simultaneously. In some embodiments, the cloransulam-methyl or salt, carboxylic acid, carboxylate salt, or ester thereof is applied at a rate from about 2.2 gai/ha to about 62 gai/ha and the compound of formula (I) or salt or ester thereof is applied at a rate from about 2 grams acid equivalent per hectare (gae/ha) to about 300 gae/ha. In some embodiments, the cloransulam-methyl or salt, carboxylic acid, carboxylate salt, or ester thereof is applied at a rate from about 1 gai/ha to about 16 gai/ha and the compound of formula (I) or salt or ester thereof is applied at a rate from about 2 g acid equivalent per hectare (gae/ha) to about 45 gae/ha. In some embodiments, the cloransulam-methyl or salt, carboxylic acid, carboxylate salt, or ester thereof is applied at a rate from about 2.19 gai/ha to about 8.75 gai/ha and the compound of formula (I) or salt or ester thereof is applied at a rate from about 4.38 g acid equivalent per hectare (gae/ha) to about 21.2 gae/ha. In some embodiments, the cloransulam-methyl or salt, carboxylic acid, carboxylate salt, or ester thereof is applied at a rate from about 2.19 gai/ha to about 35 gai/ha and the compound of formula (I) or salt or ester thereof is applied at a rate from about 4.38 g acid equivalent per hectare (gae/ha) to about 32 gae/ha. In certain embodiments, the methods utilize the compound of formula (I), or its benzyl ester and cloransulam-methyl. In one embodiment, the methods utilize the compound of formula (I) and cloransulam-methyl, wherein the compound of formula (I) is applied at a rate from about 5.3 g acid equivalent per hectare (gae/ha) to about 21.2 gae/ha, and cloransulam-methyl is applied at a rate from about 2.19 gai/ha to about 8.75 gai/ha. In one embodiment, the methods utilize the compound of formula (I) and cloransulam-methyl, wherein the compound of formula (I) is applied at a rate from about 4.38 g acid equivalent per hectare (gae/ha) to about 32 gae/ha, and cloransulam-methyl is applied at a rate from about 2.19 gai/ha to about 35 gai/ha. In one embodiment, the methods utilize the benzyl ester of the compound of formula (I) and cloransulam-methyl, wherein the benzyl ester of the compound of formula (I) is applied at a rate from about 4.38 g acid equivalent per hectare (gae/ha) to about 17.5 gae/ha, and cloransulam-methyl is applied at a rate from about 2.19 gai/ha to about 8.75 gai/ha. In one embodiment, the methods utilize the benzyl ester of the compound of formula (I) and cloransulam-methyl, wherein the benzyl ester of the compound of formula (I) is applied at a rate from about 4.38 g acid equivalent per hectare (gae/ha) to about 32 gae/ha, and cloransulam-methyl is applied at a rate from about 2.19 gai/ha to about 35 gai/ha. In certain embodiments, the methods and compositions utilizing the compound of formula (I) or salt or ester thereof in combination with cloransulam-methyl or salt, carboxylic acid, carboxylate salt, or ester thereof are used to control CYPDI, CYPIR, DIGSA, ECHCG, FIMMI, or LEFCH.

In certain embodiments of the compositions and methods described herein, the compound of formula (I) or salt or ester thereof is used in combination with diclosulam or salt thereof. With regard to the compositions, in some embodiments, the weight ratio of the compound of formula (I) or salt or ester thereof to diclosulam or salt thereof is within the range from about 1:26 to about 26:1. In certain embodiments, the weight ratio of the compound of formula (I) or salt or ester thereof to diclosulam or salt thereof is within the range from about 1:3 to about 2.6:1. In certain embodiments, the weight ratio of the compound of formula (I) or salt or ester thereof to diclosulam or salt thereof is within the range from about 1:3 to about 6:1. In certain embodiments, the weight ratio of the compound of formula (I) or salt or ester thereof to diclosulam or salt thereof is within the range from about 1:1.5 to about 3:1. In certain embodiments, the compositions provided herein comprise the compound of formula (I) or its benzyl ester and diclosulam. In one embodiment, the composition comprises the compound of formula (I) and diclosulam, wherein the weight ratio of the compound of formula (I) to diclosulam is from about 1:1.5 to about 3:1. In one embodiment, the composition comprises the benzyl ester of the compound of formula (I) and diclosulam, wherein the weight ratio of the benzyl ester of the compound of formula (I) to diclosulam is from about 1.3:1 to about 3:1. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate from about 9 grams active ingredient per hectare (gai/ha) to about 353 gai/ha based on the total amount of active ingredients in the composition. In certain embodiments, the composition is applied at an application rate from about 10 gai/ha to about 40 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and diclosulam or salt thereof, e.g., sequentially or simultaneously. In some embodiments, the diclosulam or salt thereof is applied at a rate from about 6.6 gai/ha to about 53 gai/ha and the compound of formula (I) of salt or ester thereof is applied at a rate from about 2 grams acid equivalent per hectare (gae/ha) to about 300 gae/ha. In some embodiments, the diclosulam or salt thereof is applied at a rate from about 3 gai/ha to about 26 gai/ha and the compound of formula (I) of salt or ester thereof is applied at a rate from about 2 g acid equivalent per hectare (gae/ha) to about 35 gae/ha. In some embodiments, the diclosulam or salt thereof is applied at a rate from about 6.62 gai/ha to about 13.25 gai/ha and the compound of formula (I) of salt or ester thereof is applied at a rate from about 4.38 g acid equivalent per hectare (gae/ha) to about 17.5 gae/ha. In certain embodiments, the methods utilize the compound of formula (I), or its benzyl ester and diclosulam. In one embodiment, the methods utilize the compound of formula (I) and diclosulam, wherein the compound of formula (I) is applied at a rate from about 4.38 g acid equivalent per hectare (gae/ha) to about 17.5 gae/ha, and diclosulam is applied at a rate from about 6.6 gai/ha to about 13.2 gai/ha. In one embodiment, the methods utilize the benzyl ester of the compound of formula (I) and diclosulam, wherein the benzyl ester of the compound of formula (I) is applied at a rate of about 17.5 g acid equivalent per hectare (gae/ha), and diclosulam is applied at a rate from about 6.6 gai/ha to about 13.2 gai/ha. In certain embodiments, the methods and compositions utilizing the compound of formula (I) or salt or ester thereof in combination with diclosulam or salt thereof are used to control CYPRO, ECHCG, or LEFCH.

In certain embodiments of the compositions and methods described herein, the compound of formula (I) or salt or ester thereof is used in combination with florasulam or salt thereof. With regard to the compositions, in some embodiments, the weight ratio of the compound of formula (I) or salt or ester thereof to florasulam or salt thereof is within the range from about 1:5 to about 300:1. In certain embodiments, the weight ratio of the compound of formula (I) or salt or ester thereof to florasulam or salt thereof is within the range from about 1.5:1 to about 4:1. In certain embodiments, the weight ratio of the compound of formula (I) or salt or ester thereof to florasulam or salt thereof is within the range from about 1:1.5 to about 14:1. In certain embodiments, the weight ratio of the compound of formula (I) or salt or ester thereof to florasulam or salt thereof is within the range from about 1:0.75 to about 7:1. In certain embodiments, the compositions provided herein comprise the compound of formula (I) or its benzyl ester and florasulam. In one embodiment, the composition comprises the benzyl ester of the compound of formula (I) and florasulam, wherein the weight ratio of the benzyl ester of the compound of formula (I) to florasulam is from about 1:0.75 to about 7:1. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate from about 3 grams active ingredient per hectare (gai/ha) to about 310 gai/ha based on the total amount of active ingredients in the composition. In certain embodiments, the composition is applied at an application rate from about 6 gai/ha to about 15 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and florasulam or salt thereof, e.g., sequentially or simultaneously. In some embodiments, the florasulam or salt thereof is applied at a rate from about 1.0 gai/ha to about 10 gai/ha and the compound of formula (I) of salt or ester thereof is applied at a rate from about 2 grams acid equivalent per hectare (gae/ha) to about 300 gae/ha. In some embodiments, the florasulam or salt thereof is applied at a rate from about 0.62 gai/ha to about 8 gai/ha and the compound of formula (I) of salt or ester thereof is applied at a rate from about 2.5 g acid equivalent per hectare (gae/ha) to about 18 gae/ha. In some embodiments, the florasulam or salt thereof is applied at a rate from about 1.25 gai/ha to about 3.75 gai/ha and the compound of formula (I) of salt or ester thereof is applied at a rate from about 5 g acid equivalent per hectare (gae/ha) to about 8.75 gae/ha. In certain embodiments, the methods utilize the compound of formula (I), or its benzyl ester and florasulam. In one embodiment, the methods utilize the benzyl ester of the compound of formula (I) and florasulam, wherein the benzyl ester of the compound of formula (I) is applied at a rate from about 5 g acid equivalent per hectare (gae/ha) to about 8.75 gae/ha, and florasulam is applied at a rate from about 1.25 gai/ha to about 3.75 gai/ha. In certain embodiments, the methods and compositions utilizing the compound of formula (I) or salt or ester thereof in combination with florasulam or salt thereof are used to control CIRAR, LAMPU, MATCH, SASKR, VERPE, or VIOTR.

In certain embodiments of the compositions and methods described herein, the compound of formula (I) or salt or ester thereof is used in combination with flumetsulam or salt thereof. With regard to the compositions, in some embodiments, the weight ratio of the compound of formula (I) or salt or ester thereof to flumetsulam or salt thereof is within the range from about 1:40 to about 272:1. In certain embodiments, the weight ratio of the compound of formula (I) or salt or ester thereof to flumetsulam or salt thereof is within the range from about 1:32 to about 45:1. In special embodiments, the weight ratio of the compound of formula (I) or salt or ester thereof to flumetsulam or salt thereof is within the range from about 1:3 to about 5:1. In certain embodiments, the compositions comprise the compound of formula (I) or its benzyl or n-butyl ester and flumetsulam or salt thereof. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate from about 3 grams active ingredient per hectare (gai/ha) to about 380 gai/ha based on the total amount of active ingredients in the composition. In certain embodiments, the composition is applied at an application rate from about 4 gai/ha to about 120 gai/ha based on the total amount of active ingredients in the composition. In special embodiments, the composition is applied at an application rate from about 14 gai/ha to about 57 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and flumetsulam or salt thereof, e.g., sequentially or simultaneously. In some embodiments, the flumetsulam or salt thereof is applied at a rate from about 1.1 gai/ha to about 80 gai/ha and the compound of formula (I) or salt or ester thereof is applied at a rate from about 2 grams acid equivalent per hectare (gae/ha) to about 300 gae/ha. In special embodiments, the flumetsulam or salt thereof is applied at a rate from about 6 gai/ha to about 25 gai/ha and the compound of formula (I) or salt or ester thereof is applied at a rate from about 8 grams acid equivalent per hectare (gae/ha) to about 32 gae/ha. In certain embodiments, the methods and compositions utilizing the compound of formula (I) or salt or ester thereof in combination with flumetsulam or salt thereof are used to control BRAPP or CYPIR.

In certain embodiments of the compositions and methods described herein, the compound of formula (I) or salt or ester thereof is used in combination with metosulam or salt thereof. With regard to the compositions, in some embodiments, the weight ratio of the compound of formula (I) or salt or ester thereof to metosulam or salt thereof is within the range from about 1:5 to about 300:1. In certain embodiments, the weight ratio of the compound of formula (I) or salt or ester thereof to metosulam or salt thereof is within the range from about 1:2 to about 70:1. In certain embodiments, the weight ratio of the compound of formula (I) or salt or ester thereof to metosulam or salt thereof is within the range from about 1:0.75 to about 5:1. In certain embodiments, the compositions comprise the compound of formula (I) or its benzyl or n-butyl ester and metosulam. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate from about 4 grams active ingredient per hectare (gai/ha) to about 310 gai/ha based on the total amount of active ingredients in the composition. In certain embodiments, the composition is applied at an application rate from about 6 gai/ha to about 70 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and metosulam or salt thereof, e.g., sequentially or simultaneously. In some embodiments, the metosulam or salt thereof is applied at a rate from about 2 gai/ha to about 10 gai/ha and the compound of formula (I) of salt or ester thereof is applied at a rate from about 2 grams acid equivalent per hectare (gae/ha) to about 300 gae/ha. In some embodiments, the metosulam or salt thereof is applied at a rate from about 2 gai/ha to about 10 gai/ha and the compound of formula (I) of salt or ester thereof is applied at a rate from about 8 grams acid equivalent per hectare (gae/ha) to about 32 gae/ha. In certain embodiments, the methods and compositions utilizing the compound of formula (I) or salt or ester thereof in combination with metosulam or salt thereof are used to control LEFCH.

In certain embodiments of the compositions and methods described herein, the compound of formula (I) or salt or ester thereof is used in combination with penoxsulam or salt thereof. With regard to the compositions, in some embodiments, the weight ratio of the compound of formula (I) or salt or ester thereof to penoxsulam or salt thereof is within the range from about 1:25 to about 69:1. In certain embodiments, the weight ratio of the compound of formula (I) or salt or ester thereof to penoxsulam or salt thereof is within the range from about 1:11 to about 46:1. In certain embodiments, the weight ratio of the compound of formula (I) or salt or ester thereof to penoxsulam or salt thereof is within the range from about 1:8 to about 8:1. In certain embodiments, the weight ratio of the compound of formula (I) or salt or ester thereof to penoxsulam or salt thereof is within the range from about 1:4 to about 4:1. In certain embodiments, the compositions provided herein comprise the compound of formula (I) or its benzyl or n-butyl ester and penoxsulam. In one embodiment, the composition comprises the benzyl ester of the compound of formula (I) and penoxsulam, wherein the weight ratio of the compound of formula (I) to penoxsulam is from about 1:4 to about 2:1. In one embodiment, the composition comprises the benzyl ester of the compound of formula (I) and penoxsulam, wherein the weight ratio of the benzyl ester of the compound of formula (I) to penoxsulam is from about 1:4 to about 4:1. In one embodiment, the composition comprises the benzyl ester of the compound of formula (I) and penoxsulam, wherein the weight ratio of the compound of formula (I) to penoxsulam is from about 1:11 to about 46:1. In one embodiment, the composition comprises the n-butyl ester of the compound of formula (I) and penoxsulam, wherein the weight ratio of the n-butyl ester of the compound of formula (I) to penoxsulam is from about 1:4 to about 4:1. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate from about 7 grams active ingredient per hectare (gai/ha) to about 350 gai/ha based on the total amount of active ingredients in the composition. In certain embodiments, the composition is applied at an application rate from about 9 gai/ha to about 250 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and penoxsulam or salt thereof, e.g., sequentially or simultaneously. In some embodiments, the penoxsulam or salt thereof is applied at a rate from about 7.5 gai/ha to about 50 gai/ha and the compound of formula (I) or salt or ester thereof is applied at a rate from about 2 grams acid equivalent per hectare (gae/ha) to about 300 gae/ha. In some embodiments, the penoxsulam or salt thereof is applied at a rate from about 2 gai/ha to about 100 gai/ha and the compound of formula (I) of salt or ester thereof is applied at a rate from about 2 g acid equivalent per hectare (gae/ha) to about 400 gae/ha. In some embodiments, the penoxsulam or salt thereof is applied at a rate from about 4.38 gai/ha to about 50 gai/ha and the compound of formula (I) of salt or ester thereof is applied at a rate from about 4.38 g acid equivalent per hectare (gae/ha) to about 200 gae/ha. In certain embodiments, the methods utilize the compound of formula (I), or its benzyl or n-butyl ester and penoxsulam. In one embodiment, the methods utilize the compound of formula (I) and penoxsulam, wherein the compound of formula (I) is applied at a rate from about 4.38 g acid equivalent per hectare (gae/ha) to about 35 gae/ha, and penoxsulam is applied at a rate from about 8.75 gai/ha to about 40 gai/ha. In one embodiment, the methods utilize the benzyl ester of the compound of formula (I) and penoxsulam, wherein the benzyl ester of the compound of formula (I) is applied at a rate from about 4.38 g acid equivalent per hectare (gae/ha) to about 200 gae/ha, and penoxsulam is applied at a rate from about 4.38 gai/ha to about 50 gai/ha. In one embodiment, the methods utilize the n-butyl ester of the compound of formula (I) and penoxsulam, wherein the n-butyl ester of the compound of formula (I) is applied at a rate from about 4.38 g acid equivalent per hectare (gae/ha) to about 17.5 gae/ha, and penoxsulam is applied at a rate from about 4.38 gai/ha to about 17.5 gai/ha. In certain embodiments, the methods and compositions utilizing the compound of formula (I) or salt or ester thereof in combination with penoxsulam or salt thereof are used to control BRAPP, CYPDI, CYPES, ECHCG, ECHSS, IPOHE, ISCRU, LEFCH, LEFPA, or SCPJU.

In certain embodiments of the compositions and methods described herein, the compound of formula (I) or salt or ester thereof is used in combination with pyroxsulam or salt thereof. With regard to the compositions, in some embodiments, the weight ratio of the compound of formula (I) or salt or ester thereof to pyroxsulam or salt thereof is within the range from about 1:11 to about 75:1. In certain embodiments, the weight ratio of the compound of formula (I) or salt or ester thereof to pyroxsulam or salt thereof is within the range from about 1:10 to about 3:1. In certain embodiments, the weight ratio of the compound of formula (I) or salt or ester thereof to pyroxsulam or salt thereof is within the range from about 1:1 to about 2:0.4. In certain embodiments, the weight ratio of the compound of formula (I) or salt or ester thereof to pyroxsulam or salt thereof is within the range from about 1:0.4 to about 1:0.4. In certain embodiments, the compositions provided herein comprise the compound of formula (I) or its benzyl ester and pyroxsulam. In one embodiment, the composition comprises the benzyl ester of the compound of formula (I) and pyroxsulam, wherein the weight ratio of the benzyl ester of the compound of formula (I) to pyroxsulam is about 1:0.4. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate from about 4 grams active ingredient per hectare (gai/ha) to about 362 gai/ha based on the total amount of active ingredients in the composition. In certain embodiments, the composition is applied at an application rate from about 5 gai/ha to about 22 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and pyroxsulam or salt thereof, e.g., sequentially or simultaneously. In some embodiments, the pyroxsulam or salt thereof is applied at a rate from about 3 gai/ha to about 23 gai/ha and the compound of formula (I) of salt or ester thereof is applied at a rate from about 2 grams acid equivalent per hectare (gae/ha) to about 300 gae/ha. In some embodiments, the pyroxsulam or salt thereof is applied at a rate from about 1 gai/ha to about 12 gai/ha and the compound of formula (I) of salt or ester thereof is applied at a rate from about 4 g acid equivalent per hectare (gae/ha) to about 20 gae/ha. In some embodiments, the pyroxsulam or salt thereof is applied at a rate from about 2 gai/ha to about 6 gai/ha and the compound of formula (I) of salt or ester thereof is applied at a rate from about 8 g acid equivalent per hectare (gae/ha) to about 10 gae/ha. In certain embodiments, the methods utilize the compound of formula (I), or its benzyl ester and pyroxsulam. In one embodiment, the methods utilize the benzyl ester of the compound of formula (I) and pyroxsulam, wherein the benzyl ester of the compound of formula (I) is applied at a rate of about 8.75 g acid equivalent per hectare (gae/ha), and pyroxsulam or salt thereof is applied at a rate of about 3.75 gai/ha. In certain embodiments, the methods and compositions utilizing the compound of formula (I) or salt or ester thereof in combination with pyroxsulam or salt thereof are used to control CIRAR.

The components of the mixtures described herein can be applied either separately or as part of a multipart herbicidal system.

The mixtures described herein can be applied in conjunction with one or more other herbicides to control a wider variety of undesirable vegetation. When used in conjunction with other herbicides, the composition can be formulated with the other herbicide or herbicides, tank mixed with the other herbicide or herbicides or applied sequentially with the other herbicide or herbicides. Some of the herbicides that can be employed in conjunction with the compositions and methods described herein include, but are not limited to: 4-CPA; 4-CPB; 4-CPP; 2,4-D; 2,4-D choline salt, 2,4-D esters and amines, 2,4-DB; 3,4-DA; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron-methyl, bensulide, benthiocarb, bentazon-sodium, benzadox, benzfendizone, benzipram, benzobicyclon, benzofenap, benzofluor, benzoylprop, benzthiazuron, bialaphos, bicyclopyrone, bifenox, bilanafos, bispyribac-sodium, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone-ethyl, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop-propargyl, clofop, clomazone, clomeprop, cloprop, cloproxydim, clopyralid, CMA, copper sulfate, CPMF, CPPC, credazine, cresol, cumyluron, cyanatryn, cyanazine, cycloate, cyclopyrimorate, cyclosulfamuron, cycloxydim, cycluron, cyhalofop-butyl, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop-methyl, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethbenzamide, ethametsulfuron, ethidimuron, ethiolate, ethobenzamid, etobenzamid, ethofumesate, ethoxyfen, ethoxysulfuron, etinofen, etnipromid, etobenzanid, EXD, fenasulam, fenoprop, fenoxaprop, fenoxaprop-P-ethyl, fenoxaprop-P-ethyl+isoxadifen-ethyl, fenoxasulfone, fenteracol, fenthiaprop, fentrazamide, fenuron, ferrous sulfate, flamprop, flamprop-M, flazasulfuron, fluazifop, fluazifop-P-butyl, fluazolate, flucarbazone, flucetosulfuron, fluchloralin, flufenacet, flufenican, flufenpyrethyl, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, fluorochloridone, fluoroxypyr, fluoroxypyr-meptyl, flurtamone, fluthiacet, fomesafen, foramsulfuron, fosamine, fumiclorac, furyloxyfen, glufosinate, glufosinate-ammonium, glufosinate-P-ammonium, glyphosate salts and esters, halauxifen, halauxifen-methyl, halosafen, halosulfuron-methyl, haloxydine, haloxyfop-methyl, haloxyfop-P-methyl, hexachloroacetone, hexaflurate, hexazinone, imazamethabenz, imazamox, imazapic, imazapyr, imazaquin, imazosulfuron, cloransulam-methyl, indanofan, indaziflam, iodobonil, iodomethane, iodosulfuron, iodosulfuron-ethyl-sodium, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA esters and amines, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metoxuron, metribuzin, metsulfuron, metsulfuron-methyl, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, paraflufen-ethyl, parafluoron, paraquat, pebulate, pelargonic acid, pendimethalin, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron-methyl, procyazine, prodiamine, profluazol, profluralin, profoxydim, proglinazine, prohexadione-calcium, prometon, prometryn, pronamide, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen-ethyl, pyrasulfotole, pyrazogyl, pyrazolynate, pyrazosulfuron-ethyl, pyrazoxyfen, pyribenzoxim, pyributicarb, pyriclor, pyridafol, pyridate, pyriftalid, pyriminobac, pyrimisulfan, pyrithiobac-sodium, pyroxasulfone, quinclorac, quinmerac, quinoclamine, quinonamid, quizalofop, quizalofop-P-ethyl, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosate, sulfosulfuron, sulfuric acid, sulglycapin, swep, SYN-523, TCA, tebutam, tebuthiuron, tefuryltrione, tembotrione, tepraloxydim, terbacil, terbucarb, terbuchlor, terbumeton, terbuthylazine, terbutryn, tetrafluoron, thenylchlor, thiazafluoron, thiazopyr, thidiazimin, thidiazuron, thiencarbazone-methyl, thifensulfuron, thifensulfurn-methyl, thiobencarb, tiocarbazil, tioclorim, topramezone, tralkoxydim, triafamone, tri-allate, triasulfuron, triaziflam, tribenuron, tribenuron-methyl, tricamba, triclopyr choline salt, triclopyr esters and salts, tridiphane, trietazine, trifloxysulfuron, trifluralin, triflusulfuron, trifop, trifopsime, trihydroxytriazine, trimeturon, tripropindan, tritac tritosulfuron, vernolate, xylachlor and salts, esters, optically active isomers and mixtures thereof.

The compositions and methods described herein, can further be used in conjunction with glyphosate, 5-enolpyruvylshikimate-3-phosphate (EPSP) synthase inhibitors, glufosinate, glutamine synthetase inhibitors, dicamba, phenoxy auxins, pyridyloxy auxins, synthetic auxins, auxin transport inhibitors, aryloxyphenoxypropionates, cyclohexanediones, phenylpyrazolines, acetyl CoA carboxylase (ACCase) inhibitors, imidazolinones, sulfonylureas, pyrimidinylthiobenzoates, dimethoxy-pyrimidines, triazolopyrimidines, sulfonylaminocarbonyltriazolinones, acetolactate synthase (ALS) or acetohydroxy acid synthase (AHAS) inhibitors, 4-hydroxyphenyl-pyruvate dioxygenase (HPPD) inhibitors, phytoene desaturase inhibitors, carotenoid biosynthesis inhibitors, protoporphyrinogen oxidase (PPO) inhibitors, cellulose biosynthesis inhibitors, mitosis inhibitors, microtubule inhibitors, very long chain fatty acid inhibitors, fatty acid and lipid biosynthesis inhibitors, photosystem I inhibitors, photosystem II inhibitors, triazines, and bromoxynil on glyphosate-tolerant, EPSP synthase inhibitor-tolerant, glufosinate-tolerant, glutamine synthetase inhibitor-tolerant, dicamba-tolerant, phenoxy auxin-tolerant, pyridyloxy auxin-tolerant, auxin-tolerant, auxin transport inhibitor-tolerant, aryloxyphenoxypropionate-tolerant, cyclohexanedione-tolerant, phenylpyrazoline-tolerant, ACCase-tolerant, imidazolinone-tolerant, sulfonylurea-tolerant, pyrimidinylthiobenzoate-tolerant, triazolopyrimidine-tolerant, sulfonylaminocarbonyltriazolinone-tolerant, ALS- or AHAS-tolerant, HPPD-tolerant, phytoene desaturase inhibitor-tolerant, carotenoid biosynthesis inhibitor tolerant, PPO-tolerant, cellulose biosynthesis inhibitor-tolerant, mitosis inhibitor-tolerant, microtubule inhibitor-tolerant, very long chain fatty acid inhibitor-tolerant, fatty acid and lipid biosynthesis inhibitor-tolerant, photosystem I inhibitor-tolerant, photosystem II inhibitor-tolerant, triazine-tolerant, bromoxynil-tolerant, and crops possessing multiple or stacked traits conferring tolerance to multiple chemistries and/or multiple modes of action via single and/or multiple resistance mechanisms. In some embodiments, the compound of formula (I) or salt or ester thereof and complementary herbicide or salt or ester thereof are used in combination with herbicides that are selective for the crop being treated and which complement the spectrum of weeds controlled by these compounds at the application rate employed. In some embodiments, the compositions described herein and other complementary herbicides are applied at the same time, either as a combination formulation, as a tank mix or sequentially.

In some embodiments, the compositions described herein are employed in combination with one or more herbicide safeners, such as AD-67 (MON 4660), benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, harpin proteins, isoxadifen-ethyl, jiecaowan, jiecaoxi, mefenpyr-diethyl, mephenate, naphthalic anhydride (NA), oxabetrinil, 829148 and N-phenyl-sulfonylbenzoic acid amides, to enhance their selectivity. In some embodiments, the safeners are employed in rice, cereal, corn, or maize settings. In some embodiments, the safener is cloquintocet or an ester or salt thereof. In certain embodiments, cloquintocet is utilized to antagonize harmful effects of the compositions on rice and cereals. In some embodiments, the safener is cloquintocet (mexyl).

In some embodiments, the compositions described herein are employed in combination with one or more plant growth regulators, such as 2,3,5-tri-iodobenzoic acid, IAA, IBA, naphthaleneacetamide, α-naphthaleneacetic acids, benzyladenine, 4-hydroxyphenethyl alcohol, kinetin, zeatin, endothal, ethephon, pentachlorophenol, thidiazuron, tribufos, aviglycine, ethephon, maleic hydrazide, gibberellins, gibberellic acid, abscisic acid, ancymidol, fosamine, glyphosine, isopyrimol, jasmonic acid, maleic hydrazide, mepiquat, 2,3,5-triiodobenzoic acid, morphactins, dichlorflurenol, flurprimidol, mefluidide, paclobutrazol, tetcyclacis, uniconazole, brassinolide, brassinolide-ethyl, cycloheximide, ethylene, methasulfocarb, prohexadione, triapenthenol and trinexapac.

In some embodiments, the plant growth regulators are employed in one or more crops or settings, such as rice, cereal crops, corn, maize, broadleaf crops, oilseed rape/canola, turf, pineapple, sugarcane, sunflower, pastures, grasslands, rangelands, fallowland, tree and vine orchards, plantation crops, vegetables, and non-crop (ornamentals) settings. In some embodiments, the plant growth regulator is mixed with the compound of formula (I), or mixed with the compound of formula (I) and a triazolopyrimidine sulfonamide to cause a preferentially advantageous effect on plants.

In some embodiments, compositions provided herein further comprise at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water-dispersible granules, or wettable powders, or liquids, such as, for example, emulsifiable concentrates, solutions, emulsions or suspensions. They can also be provided as a pre-mix or tank mixed.

Suitable agricultural adjuvants and carriers include, but are not limited to, crop oil concentrate; nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99.

Liquid carriers that can be employed include water and organic solvents. The organic solvents include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like. Specific organic solvents include, but are not limited to toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. In certain embodiments, Water is the carrier for the dilution of concentrates.

Suitable solid carriers include but are not limited to talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, cellulose, and the like.

In some embodiments, the compositions described herein further comprise one or more surface-active agents. In some embodiments, such surface-active agents are employed in both solid and liquid compositions, and in certain embodiments those designed to be diluted with carrier before application. The surface-active agents can be anionic, cationic or nonionic in character and can be employed as emulsifying agents, wetting agents, suspending agents, or for other purposes. Surfactants which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Surface-active agents include, but are not limited to salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkyl-naphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, and in certain embodiments, methyl esters.

In some embodiments, these materials, such as vegetable or seed oils and their esters, can be used interchangeably as an agricultural adjuvant, as a liquid carrier or as a surface active agent.

Other exemplary additives for use in the compositions provided herein include but are not limited to compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

In some embodiments, the concentration of the active ingredients in the compositions described herein is from about 0.0005 to 98 percent by weight. In some embodiments, the concentration is from about 0.0006 to 90 percent by weight. In compositions designed to be employed as concentrates, the active ingredients, in certain embodiments, are present in a concentration from about 0.1 to 98 weight percent, and in certain embodiments about 0.5 to 90 weight percent. Such compositions are, in certain embodiments, diluted with an inert carrier, such as water, before application. The diluted compositions usually applied to weeds or the locus of weeds contain, in certain embodiments, about 0.0003 to 1.5 weight percent active ingredient and in certain embodiments contain about 0.0008 to 1.0 weight percent.

The present compositions can be applied to weeds or their locus by the use of conventional ground or aerial dusters, sprayers, and granule applicators, by addition to irrigation or paddy water, and by other conventional means known to those skilled in the art.

The described embodiments and following examples are for illustrative purposes and are not intended to limit the scope of the claims. Other modifications, uses, or combinations with respect to the compositions described herein will be apparent to a person of ordinary skill in the art without departing from the spirit and scope of the claimed subject matter.

EXAMPLES

Example I

Evaluation of Postemergence Foliar-Applied Herbicidal Mixtures for Weed Control in Direct Seeded Rice in the Greenhouse Seeds or nutlets of the desired test plant species were planted in a soil matrix prepared by mixing a loam or sandy loam soil (e.g., 28.6 percent silt, 18.8 percent clay, and 52.6 percent sand, with a pH of about 5.8 and an organic matter content of about 1.8 percent) and calcareous grit in an 80 to 20 ratio. The soil matrix was contained in plastic pots with a volume of 1 quart and a surface area of 83.6 square centimeters (cm$^2$). When required to ensure good germination and healthy plants, a fungicide treatment and/or other chemical or physical treatment was applied. The plants were grown for 8-22 days in a greenhouse with an approximate 14 h photoperiod which was maintained at about 29° C. during the day and about 26° C. during the night. Nutrients (Peters Excel® 15-5-15 5-Ca 2-Mg and iron chelate) were applied in the irrigation solution as needed and water was added on a regular basis. Supplemental lighting was provided with overhead metal halide 1000-Watt lamps as necessary. The plants were employed for testing when they reached the first through fourth true leaf stage.

Treatments consisted of the acid or esters of 4-amino-3-chloro-5-fluoro-6-(4-chloro-2-fluoro-3-methoxy-phenyl)pyridine-2-carboxylic acid (Compound A), each formulated as an SC (suspension concentrate), and various herbicidal components alone and in combination. Forms of compound A were applied on an acid equivalent basis.

Forms of compound A (compound of formula I) tested include:

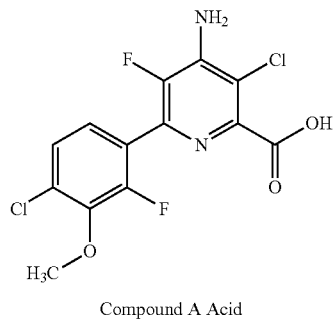

Compound A Acid

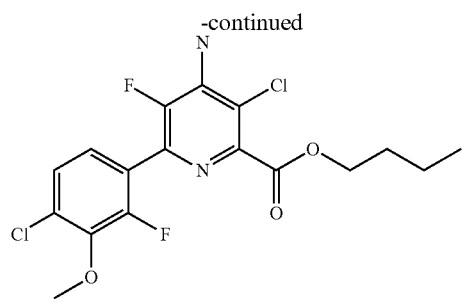

Compound A n-Butyl Ester

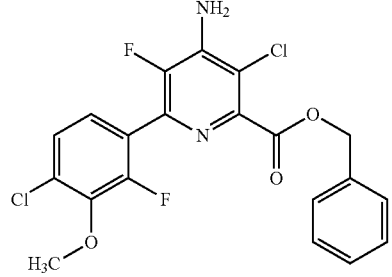

Compound A Benzyl Ester

Other herbicidal components were applied on an active ingredient basis and included acetolactate synthase (ALS)-inhibiting herbicides (sulfonamide chemical class) penoxsulam formulated as Grasp® SC, diclosulam formulated as Strongarm®, and cloransulam-methyl formulated as FirstRate®, flumetsulam formulated as Flumetsulam WG, and metosulam formulated as Eclipse®.

Treatment requirements were calculated based upon the rates being tested, the concentration of active ingredient or acid equivalent in the formulation, and a 12 mL application volume at a rate of 187 L/ha.

For treatments comprised of formulated compounds, measured amounts of compounds were placed individually in 25 mL glass vials and diluted in a volume of 1.25% (v/v) Agri-Dex® crop oil concentrated to obtain 12× stock solutions. If a test compound did not dissolve readily, the mixture was warmed and/or sonicated. Application solutions were prepared by adding an appropriate amount of each stock solution (e.g., 1 mL) and diluted to the appropriate final concentrations with the addition of 10 mL of an aqueous mixture of 1.25% (v/v) crop oil concentrate so that the final spray solutions contained 1.25+/−0.05% (v/v) crop oil concentrate.

For treatments comprised of technical compounds, weighed amounts can be placed individually in 25 mL glass vials and dissolved in a volume of 97:3 v/v acetone/DMSO to obtain 12× stock solutions. If a test compound does not dissolve readily, the mixture can be warmed and/or sonicated. Application solutions can be prepared by adding an appropriate amount of each stock solution (e.g., 1 mL) and diluted to the appropriate final concentrations with the addition of 10 mL of an aqueous mixture of 1.5% (v/v) crop oil concentrate so that the final spray solutions contain 1.25% (v/v) crop oil concentrate. When technical materials are used, the concentrated stock solutions can be added to the spray solutions so that the final acetone and DMSO concentrations of the application solutions are 16.2% and 0.5%, respectively.

For treatments comprised of formulated and technical compounds, weighed amounts of the technical materials can be placed individually in 25 mL glass vials and dissolved in a volume of 97:3 v/v acetone/DMSO to obtain 12× stock solutions, and measured amounts of the formulated compounds can be placed individually in 25 mL glass vials and diluted in a volume of 1.5% (v/v) crop oil concentrate or water to obtain 12× stock solutions. If a test compound does not dissolve readily, the mixture can be warmed and/or sonicated. Application solutions can be prepared by adding an appropriate amount of each stock solution (e.g., 1 mL) and diluted to the appropriate final concentrations with the addition of an appropriate amount of an aqueous mixture of 1.5% (v/v) crop oil concentrate or water so that the final spray solutions contain 1.25% (v/v) crop oil concentrate. As required, additional water and/or 97:3 v/v acetone/DMSO can be added to individual application solutions so that the final acetone and DMSO concentrations of the application solutions being compared are 8.1% and 0.25%, respectively.

All stock solutions and applications solutions were visually inspected for compound compatibility prior to application. Spray solutions were applied to the plant material with an overhead Mandel track sprayer equipped with an 8002E nozzle calibrated to deliver 187 L/ha over an application area of 0.503 m² at a spray height of 18 to 20 inches (46 to 50 cm) above average plant canopy height. Control plants were sprayed in the same manner with the solvent blank.

The treated plants and control plants were placed in a greenhouse as described above and watered by sub-irrigation to prevent wash-off of the test compounds. After approximately 3 weeks, the condition of the test plants as compared with that of the untreated plants was determined visually and scored on a scale of 0 to 100 percent where 0 corresponds to no injury or growth inhibition and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22.).

The following equation was used to calculate the expected activity of mixtures containing two active ingredients, A and B:

$$\text{Expected} = A + B - (A \times B/100)$$

A=observed efficacy of active ingredient A at the same concentration as used in the mixture.
B=observed efficacy of active ingredient B at the same concentration as used in the mixture.

The compounds tested, application rates employed, plant species tested, and results are given in Tables 1-9.

TABLE 1

Synergistic Activity of Foliar-Applied Compound A Acid and Penoxsulam Herbicidal Compositions on Weed Control in a Rice Cropping System.

| Compound A Acid gae/ha | Penoxsulam gai/ha | Obs | Exp |
|---|---|---|---|
| \multicolumn{4}{c}{Visual Weed Control (%) - 27 DAA IPOHE} | | | |
| 4.38 | 0 | 10 | — |
| 8.75 | 0 | 10 | — |
| 17.5 | 0 | 10 | — |
| 0 | 8.75 | 15 | — |
| 0 | 17.5 | 20 | — |
| 4.38 | 8.75 | 95 | 24 |
| 8.75 | 8.75 | 60 | 24 |
| 17.5 | 8.75 | 20 | 24 |
| 4.38 | 17.5 | 95 | 28 |
| 8.75 | 17.5 | 20 | 28 |
| 17.5 | 17.5 | 40 | 28 |

TABLE 1-continued

Synergistic Activity of Foliar-Applied Compound A Acid and Penoxsulam Herbicidal Compositions on Weed Control in a Rice Cropping System.

| Compound A Acid gae/ha | Penoxsulam gai/ha | Obs | Exp |
|---|---|---|---|
| Visual Weed Control (%) - 19 DAA LEFCH | | | |
| 19.4 | 0 | 5 | — |
| 0 | 40 | 0 | — |
| 19.4 | 40 | 30 | 5 |

TABLE 2

Synergistic Activity of Foliar-Applied Compound A n-Butyl Ester and Penoxsulam Herbicidal Compositions on Weed Control in a Rice Cropping System.

| Compound A n-Butyl Ester gae/ha | Penoxsulam gai/ha | Obs | Exp |
|---|---|---|---|
| Visual Weed Control (%) - 21 DAA BRAPP | | | |
| 4.38 | 0 | 0 | — |
| 8.75 | 0 | 40 | — |
| 0 | 4.38 | 0 | — |
| 0 | 8.75 | 20 | — |
| 4.38 | 4.38 | 40 | 0 |
| 8.75 | 4.38 | 40 | 40 |
| 4.38 | 8.75 | 50 | 20 |
| 8.75 | 8.75 | 60 | 52 |
| Visual Weed Control (%) - 27 DAA ECHCG | | | |
| 4.38 | 0 | 0 | — |
| 8.75 | 0 | 0 | — |
| 17.5 | 0 | 90 | — |
| 0 | 4.38 | 0 | — |
| 0 | 8.75 | 30 | — |
| 4.38 | 4.38 | 60 | 0 |
| 8.75 | 4.38 | 70 | 0 |
| 17.5 | 4.38 | 95 | 90 |
| 4.38 | 8.75 | 95 | 30 |
| 8.75 | 8.75 | 80 | 30 |
| 17.5 | 8.75 | 90 | 93 |
| Visual Weed Control (%) - 27 DAA IPOHE | | | |
| 4.38 | 0 | 10 | — |
| 8.75 | 0 | 10 | — |
| 17.5 | 0 | 10 | — |
| 0 | 8.75 | 15 | — |
| 0 | 17.5 | 20 | — |
| 4.38 | 8.75 | 95 | 24 |
| 8.75 | 8.75 | 95 | 24 |
| 17.5 | 8.75 | 50 | 24 |
| 4.38 | 17.5 | 100 | 28 |
| 8.75 | 17.5 | 50 | 28 |
| 17.5 | 17.5 | 95 | 28 |

TABLE 3

Synergistic Activity of Foliar-Applied Compound A Benzyl Ester and Penoxsulam Herbicidal Compositions on Weed Control in a Rice Cropping System.

| Compound A Benzyl Ester gae/ha | Penoxsulam gai/ha | Obs | Exp |
|---|---|---|---|
| | | Visual Weed Control (%) - 21 DAA BRAPP | |
| 17.5 | 0 | 80 | — |
| 0 | 4.38 | 0 | — |
| 0 | 8.75 | 20 | — |
| 0 | 17.5 | 40 | — |
| 17.5 | 4.38 | 95 | 80 |
| 17.5 | 8.75 | 95 | 84 |
| 17.5 | 17.5 | 95 | 88 |
| | | Visual Weed Control (%) - 27 DAA IPOHE | |
| 4.38 | 0 | 10 | — |
| 8.75 | 0 | 10 | — |
| 17.5 | 0 | 10 | — |
| 0 | 4.38 | 10 | — |
| 0 | 8.75 | 15 | — |
| 0 | 17.5 | 20 | — |
| 4.38 | 4.38 | 50 | 19 |
| 8.75 | 4.38 | 40 | 19 |
| 17.5 | 4.38 | 95 | 19 |
| 4.38 | 8.75 | 50 | 24 |
| 8.75 | 8.75 | 95 | 24 |
| 17.5 | 8.75 | 40 | 24 |
| 4.38 | 17.5 | 100 | 28 |
| 8.75 | 17.5 | 60 | 28 |
| 17.5 | 17.5 | 70 | 28 |
| | | Visual Weed Control (%) - 21 DAA ISCRU | |
| 8 | 0 | 20 | — |
| 16 | 0 | 0 | — |
| 0 | 10 | 0 | — |
| 0 | 20 | 0 | — |
| 8 | 10 | 100 | 20 |
| 16 | 10 | 100 | 0 |
| 8 | 20 | 15 | 20 |
| 16 | 20 | 100 | 0 |

TABLE 4

Synergistic Activity of Foliar-Applied Compound A Acid and Diclosulam Herbicidal Compositions on Control of Weeds Common to Rice Cropping Systems.

| Compound A Acid gae/ha | Diclosulam gai/ha | Obs | Exp |
|---|---|---|---|
| | | Visual Weed Control (%) - 20 DAA LEFCH | |
| 4.38 | 0 | 15 | — |
| 8.75 | 0 | 30 | — |
| 17.5 | 0 | 50 | — |
| 0 | 6.62 | 0 | — |
| 4.38 | 6.62 | 55 | 15 |
| 8.75 | 6.62 | 50 | 30 |
| 17.5 | 6.62 | 55 | 50 |

TABLE 5

Synergistic Activity of Foliar-Applied Compound A Benzyl Ester and Diclosulam Herbicidal Compositions on Control of Weeds Common to Rice Cropping Systems.

| Compound A Benzyl Ester gae/ha | Diclosulam gai/ha | Visual Weed Control (%) - 20 DAA LEFCH | |
|---|---|---|---|
| | | Obs | Exp |
| 17.5 | 0 | 60 | — |
| 0 | 6.62 | 0 | — |
| 0 | 13.25 | 20 | — |
| 17.5 | 6.62 | 75 | 60 |
| 17.5 | 13.25 | 70 | 68 |

TABLE 6

Synergistic Activity of Foliar-Applied Compound A Acid and Cloransulam-methyl Herbicidal Compositions on Control of Weeds Common to Rice Cropping Systems.

| Compound A Acid gae/ha | Cloransulam-methyl gai/ha | Visual Weed Control (%) - 20 DAA DIGSA | |
|---|---|---|---|
| | | Obs | Exp |
| 5.3 | 0 | 10 | — |
| 10.6 | 0 | 20 | — |
| 21.2 | 0 | 20 | — |
| 0 | 2.19 | 10 | — |
| 5.3 | 2.19 | 45 | 19 |
| 10.6 | 2.19 | 30 | 28 |
| 21.2 | 2.19 | 40 | 28 |

| Compound A Acid gae/ha | Cloransulam-methyl gai/ha | Visual Weed Control (%) - 20 DAA LEFCH | |
|---|---|---|---|
| | | Obs | Exp |
| 5.3 | 0 | 0 | — |
| 10.6 | 0 | 10 | — |
| 21.2 | 0 | 15 | — |
| 0 | 4.38 | 0 | — |
| 0 | 8.75 | 0 | — |
| 5.3 | 4.38 | 15 | 0 |
| 10.6 | 4.38 | 15 | 10 |
| 21.2 | 4.38 | 90 | 15 |
| 5.3 | 8.75 | 50 | 0 |
| 10.6 | 8.75 | 10 | 10 |
| 21.2 | 8.75 | 75 | 15 |

TABLE 7

Synergistic Activity of Foliar-Applied Compound A Benzyl Ester and Cloransulam-methyl Herbicidal Compositions on Control of Weeds Common to Rice Cropping Systems.

| Compound A Benzyl Ester gae/ha | Cloransulam-methyl gai/ha | Visual Weed Control (%) - 20 DAA LEFCH | |
|---|---|---|---|
| | | Obs | Exp |
| 4.38 | 0 | 10 | — |
| 8.75 | 0 | 20 | — |
| 0 | 2.19 | 0 | — |
| 0 | 4.38 | 0 | — |
| 4.38 | 2.19 | 25 | 10 |

TABLE 7-continued

Synergistic Activity of Foliar-Applied Compound A Benzyl
Ester and Cloransulam-methyl Herbicidal Compositions
on Control of Weeds Common to Rice Cropping Systems.

| 8.75 | 2.19 | 15 | 20 |
| 4.38 | 4.38 | 15 | 10 |
| 8.75 | 4.38 | 50 | 20 |

| Compound A Benzyl Ester | Cloransulam-methyl | Visual Weed Control (%) - 20 DAA CYPIR | |
|---|---|---|---|
| gae/ha | gai/ha | Obs | Exp |
| 4.38 | 0 | 15 | — |
| 8.75 | 0 | 60 | — |
| 17.5 | 0 | 90 | — |
| 0 | 4.38 | 70 | — |
| 0 | 8.75 | 85 | — |
| 4.38 | 4.38 | 90 | 75 |
| 8.75 | 4.38 | 100 | 88 |
| 17.5 | 4.38 | 90 | 97 |
| 4.38 | 8.75 | 99 | 87 |
| 8.75 | 8.75 | 95 | 94 |
| 17.5 | 8.75 | 100 | 99 |

TABLE 8

Synergistic Activity of Foliar-Applied Compound A Benzyl
Ester and Flumetsulam Herbicidal Compositions on
Control of Weeds Common to Rice Cropping Systems.

| Compound A Benzyl Ester | Flumetsulam | Visual Weed Control (%) - 22 DAA BRAPP | |
|---|---|---|---|
| gae/ha | gai/ha | Obs | Exp |
| 8 | 0 | 60 | — |
| 16 | 0 | 60 | — |
| 32 | 0 | 90 | — |
| 0 | 6.25 | 30 | — |
| 8 | 6.25 | 85 | 72 |
| 16 | 6.25 | 80 | 72 |
| 32 | 6.25 | 95 | 93 |

| Compound A Benzyl Ester | Flumetsulam | Visual Weed Control (%) - 22 DAA CYPIR | |
|---|---|---|---|
| gae/ha | gai/ha | Obs | Exp |
| 8 | 0 | 20 | — |
| 16 | 0 | 85 | — |
| 0 | 6.25 | 20 | — |
| 0 | 12.5 | 55 | — |
| 0 | 25 | 30 | — |
| 8 | 6.25 | 100 | 36 |
| 16 | 6.25 | 100 | 88 |
| 8 | 12.5 | 60 | 64 |
| 16 | 12.5 | 100 | 93 |
| 8 | 25 | 70 | 44 |
| 16 | 25 | 100 | 90 |

TABLE 9

Synergistic Activity of Foliar-Applied Compound A Benzyl Ester
and Metosulam Herbicidal Compositions on Control of Weeds
Common to Rice Cropping Systems.

| Compound A Benzyl Ester | Metosulam | Visual Weed Control (%) - 22 DAA LEFCH | |
|---|---|---|---|
| gae/ha | gai/ha | Obs | Exp |
| 8 | 0 | 10 | — |
| 16 | 0 | 25 | — |
| 32 | 0 | 55 | — |
| 0 | 6.25 | 15 | — |
| 8 | 6.25 | 45 | 24 |
| 16 | 6.25 | 40 | 36 |
| 32 | 6.25 | 65 | 62 |

| | | |
|---|---|---|
| BRAPP | *Brachiaria platyphylla* (Griseb.) Nash or *Urochloa platyphylla* (Nash) R.D. Webster | signalgrass, broadleaf |
| CYPIR | *Cyperus iria* L. | flatsedge, rice |
| DIGSA | *Digitaria sanguinalis* (L.) Scop. | crabgrass, large |
| ECHCG | *Echinochloa crusgalli* (L.) Beauv. | barnyardgrass |
| IPOHE | *Ipomoea hederacea* Jacq. | morningglory, ivyleaf |
| ISCRU | *Ischaemum rugosum* Salisb. | saramollagrass |
| LEFCH | *Leptochloa chinensis* (L.) Nees | sprangletop, Chinese | gae/ha = grams acid equivalent per hectare
gai/ha = grams active ingredient per hectare
Obs = observed value
Exp = expected value as calculated by Colby's equation
DAA = days after application Example II Evaluation of in-Water Applied Herbicidal Mixtures for Weed Control in Transplanted Paddy Rice in the Greenhouse Weed seeds or nutlets of the desired test plant species were planted in puddled soil (mud) prepared by mixing a shredded, non-sterilized mineral soil (50.5 percent silt, 25.5 percent clay, and 24 percent sand, with a pH of about 7.6 and an organic matter content of about 2.9 percent) and water at a 1:1 volumetric ratio. The prepared mud was dispensed in 365 mL aliquots into 16-ounce (oz.) non-perforated plastic pots with a surface area of 86.59 square centimeters ($cm^2$) leaving a headspace of 3 centimeters in each pot. Mud was allowed to dry overnight prior to planting or transplanting. Rice seeds were planted in Sun Gro MetroMix® 306 planting mixture, which typically has a pH of 6.0 to 6.8 and an organic matter content of about 30 percent, in plastic plug trays. Seedlings at the second or third leaf stage of growth were transplanted into 840 mL of mud contained in 32-oz. non-perforated plastic pots with a surface area of 86.59 $cm^2$ 4 days prior to herbicide application. The paddy was created by filling the headspace of the pots with 2.5 to 3 cm of water. When required to ensure good germination and healthy plants, a fungicide treatment and/or other chemical or physical treatment was applied. The plants were grown for 4-22 days in a greenhouse with an approximate 14 h photoperiod which was maintained at about 29'C during the day and about 26° C. during the night. Nutrients were added as Osmocote® (19:6:12, N:P:K+minor nutrients) at 2 g per 16-oz. pot and 4 g per 32-oz. pot. Water was added on a regular basis to maintain the paddy flood, and supplemental lighting was provided with overhead metal halide 1000-Watt lamps as necessary. The plants were employed for testing when they reached the first through fourth true leaf stage.

Treatments consisted of the acid or esters of 4-amino-3-chloro-5-fluoro-6-(4-chloro-2-fluoro-3-methoxy-phenyl) pyridine-2-carboxylic acid (compound A) each formulated as an SC and various herbicidal components alone and in combination. Forms of compound A were applied on an acid equivalent basis.

Forms of compound A (compound of formula I) tested include:

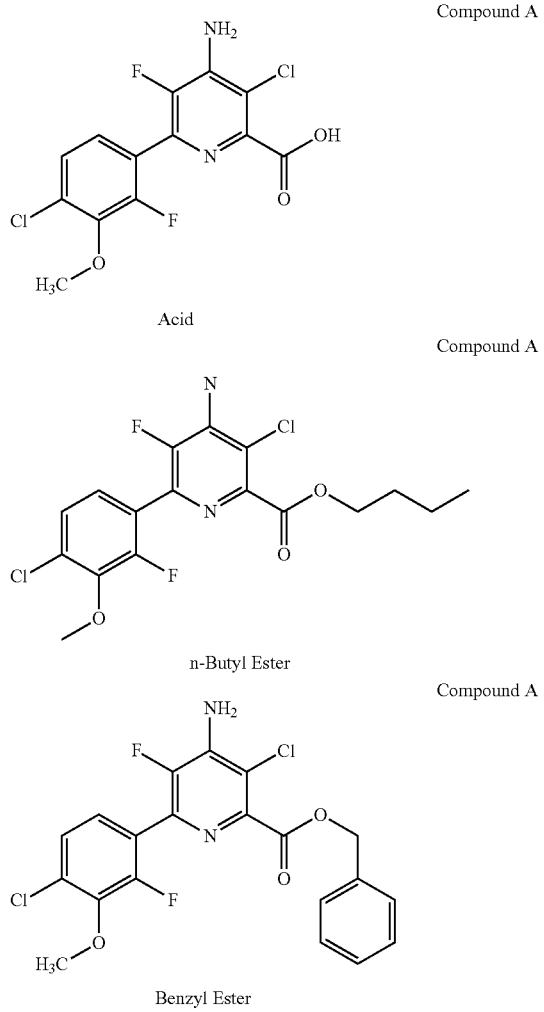

Compound A

Acid

Compound A n-Butyl Ester

Compound A

Benzyl Ester

Other herbicidal components were applied on an active ingredient basis and included acetolactate synthase (ALS)-inhibiting herbicides (sulfonamide chemical class) penoxsulam formulated as Grasp® SC (GF-443), diclosulam formulated as Strongarm®, and cloransulam-methyl formulated as FirstRate®.

Treatment requirements for each compound or herbicidal component were calculated based upon the rates being tested, the concentration of active ingredient or acid equivalent in the formulation, an application volume of 2 mL per component per pot, and an application area of 86.59 cm² per pot.

For formulated compounds, a measured amount was placed in an individual 100 or 200 mL glass vial and was dissolved in a volume of 1.25% (v/v) Agri-Dex® crop oil concentrate to obtain each application solution. If the test compound did not dissolve readily, the mixture was warmed and/or sonicated.

For technical grade compounds, a weighed amount can be placed in an individual 100 to 200 mL glass vial and dissolved in a volume of acetone to obtain a concentrated stock solution. If the test compound does not dissolve readily, the mixture can be warmed and/or sonicated. The concentrated stock solutions obtained can be diluted with an equivalent volume of an aqueous mixture containing 2.5% (v/v) crop oil concentrate so that the final application solutions contain 1.25% (v/v) crop oil concentrate.

Applications were made by injecting with a pipetter appropriate amounts of the application solutions, individually and sequentially, into the aqueous layer of the paddy. Control plants were treated in the same manner with the solvent blank. Applications were made so that all treated plant material received the same concentrations of acetone and crop oil concentrate.

The treated plants and control plants were placed in a greenhouse as described above and water was added as needed to maintain a paddy flood. After approximately 3 weeks the condition of the test plants as compared with that of the untreated plants was determined visually and scored on a scale of 0 to 100 percent where 0 corresponds to no injury or growth inhibition and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22.).

The following equation was used to calculate the expected activity of mixtures containing two active ingredients, A and B:

$$\text{Expected} = A + B - (A \times B / 100)$$

A=observed efficacy of active ingredient A at the same concentration as used in the mixture.

B=observed efficacy of active ingredient B at the same concentration as used in the mixture.

Some of the compounds tested, application rates employed, plant species tested, and results are given in Tables 10-15.

TABLE 10

Synergistic Activity of In-Water Applications of Compound A Acid and Penoxsulam Herbicidal Compositions on Weed Control in a Rice Cropping System.

| Compound A Acid | Penoxsulam | Visual Weed Control (%) - 25 DAA LEFCH | |
|---|---|---|---|
| gae/ha | gai/ha | Obs | Exp |
| 8.75 | 0 | 50 | — |
| 17.5 | 0 | 50 | — |
| 35 | 0 | 85 | — |
| 0 | 35 | 40 | — |
| 8.75 | 35 | 100 | 70 |
| 17.5 | 35 | 100 | 70 |
| 35 | 35 | 100 | 91 |

TABLE 11

Synergistic Activity of In-Water Applications of Compound A Benzyl Ester and Penoxsulam Herbicidal Compositions on Weed Control in a Rice Cropping System.

| Compound A Benzyl Ester | Penoxsulam | Visual Weed Control (%) - 25 DAA LEFCH | |
|---|---|---|---|
| gae/ha | gai/ha | Obs | Exp |
| 8.75 | 0 | 50 | — |
| 17.5 | 0 | 90 | — |
| 0 | 17.5 | 0 | — |
| 0 | 35 | 40 | — |
| 8.75 | 17.5 | 90 | 50 |
| 17.5 | 17.5 | 99 | 90 |
| 8.75 | 35 | 100 | 70 |
| 17.5 | 35 | 100 | 94 |

| Compound A Benzyl Ester | Penoxsulam | Visual Weed Control (%) - 21 DAA SCPMA | |
|---|---|---|---|
| gae/ha | gai/ha | Obs | Exp |
| 48 | 0 | 0 | — |
| 96 | 0 | 0 | — |
| 0 | 10 | 70 | — |
| 0 | 20 | 88 | — |
| 0 | 40 | 95 | — |
| 48 | 10 | 75 | 70 |
| 96 | 10 | 90 | 70 |
| 48 | 20 | 85 | 88 |
| 96 | 20 | 100 | 88 |
| 48 | 40 | 100 | 95 |
| 96 | 40 | 99 | 95 |

TABLE 12

Synergistic Activity of In-Water Applications of Compound A Acid and Diclosulam Herbicidal Compositions on Control of Weeds Common to Rice Cropping Systems.

| Compound A Acid | Diclosulam | Visual Weed Control (%) - 21 DAA CYPRO | |
|---|---|---|---|
| gae/ha | gai/ha | Obs | Exp |
| 8.75 | 0 | 0 | — |
| 0 | 6.62 | 80 | — |
| 0 | 13.25 | 80 | — |
| 8.75 | 6.62 | 100 | 80 |
| 8.75 | 13.25 | 95 | 80 |

TABLE 13

Synergistic Activity of In-Water Applications of Compound A Benzyl Ester and Diclosulam Herbicidal Compositions on Control of Weeds Common to Rice Cropping Systems.

| Compound A Benzyl Ester | Diclosulam | Visual Weed Control (%) - 21 DAA ECHCG | |
|---|---|---|---|
| gae/ha | gai/ha | Obs | Exp |
| 4.38 | 0 | 20 | — |
| 8.75 | 0 | 85 | — |
| 0 | 6.62 | 70 | — |
| 4.38 | 6.62 | 100 | 76 |

TABLE 13-continued

Synergistic Activity of In-Water Applications of Compound A Benzyl Ester and Diclosulam Herbicidal Compositions on Control of Weeds Common to Rice Cropping Systems.

| Compound A Benzyl Ester | Diclosulam | Visual Weed Control (%) - 21 DAA ECHCG | |
|---|---|---|---|
| gae/ha | gai/ha | Obs | Exp |
| 8.75 | 6.62 | 100 | 96 |

TABLE 14

Synergistic Activity of In-Water Applications of Compound A Acid and Chloransulam-methyl Herbicidal Compositions on Control of Weeds Common to Rice Cropping Systems.

| Compound A Acid | Cloransulam-methyl | Visual Weed Control (%) - 22 DAA ECHCG | |
|---|---|---|---|
| gae/ha | gai/ha | Obs | Exp |
| 16 | 0 | 20 | — |
| 32 | 0 | 25 | — |
| 0 | 17.5 | 50 | — |
| 16 | 17.5 | 75 | 60 |
| 32 | 17.5 | 75 | 63 |

| Compound A Acid | Cloransulam-methyl | Visual Weed Control (%) - 21 DAA CYPDI | |
|---|---|---|---|
| gae/ha | gai/ha | Obs | Exp |
| 16 | 0 | 30 | — |
| 0 | 17.5 | 40 | — |
| 0 | 35 | 80 | — |
| 16 | 17.5 | 99 | 58 |
| 16 | 35 | 100 | 86 |

| Compound A Acid | Cloransulam-methyl | Visual Weed Control (%) - 21 DAA FIMMI | |
|---|---|---|---|
| gae/ha | gai/ha | Obs | Exp |
| 16 | 0 | 20 | — |
| 32 | 0 | 20 | — |
| 0 | 17.5 | 40 | — |
| 0 | 35 | 60 | — |
| 16 | 17.5 | 100 | 52 |
| 32 | 17.5 | 100 | 52 |
| 16 | 35 | 75 | 68 |
| 32 | 35 | 90 | 68 |

TABLE 15

Synergistic Activity of In-Water Applications of Compound A Benzyl Ester and Chloransulam-methyl Herbicidal Compositions on Control of Weeds Common to Rice Cropping Systems.

| Compound A Benzyl Ester | Cloransulam-methyl | Visual Weed Control (%) - 21 DAA FIMMI | |
|---|---|---|---|
| gae/ha | gai/ha | Obs | Exp |
| 8 | 0 | 30 | — |
| 0 | 17.5 | 40 | — |
| 0 | 35 | 60 | — |
| 8 | 17.5 | 90 | 58 |
| 8 | 35 | 100 | 72 |

| | | |
|---|---|---|
| CYPDI | *Cyperus difformis* L. | sedge, smallflower umbrella |
| CYPRO | *Cyperus rotundus* L. | nutsedge, purple |
| ECHCG | *Echinochloa crusgalli* (L.) Beauv. | barnyardgrass |
| FIMMI | *Fimbristylis miliacea* (L.) Vahl | fringerush, globe |
| LEFCH | *Leptochloa chinensis* (L.) Nees | sprangletop, Chinese | gae/ha = grams acid equivalent per hectare
gai/ha = grams active ingredient per hectare
Obs = observed value
Exp = expected value as calculated by Colby's equation
DAA = days after application

Example III

Evaluation of Postemergence Foliar-Applied Herbicidal Mixtures for Weed Control in Cereal Crops in the Greenhouse Seeds of the desired test plant species were planted in Sun Gro MetroMix® 306 planting mixture, which typically has a pH of 6.0 to 6.8 and an organic matter content of about 30 percent, in plastic pots with a surface area of 103.2 square centimeters (cm²). When required to ensure good germination and healthy plants, a fungicide treatment and/or other chemical or physical treatment was applied. The plants were grown for 7-36 days in a greenhouse with an approximate 14 hour photoperiod which was maintained at about 18° C. during the day and about 17° C. during the night. Nutrients and water were added on a regular basis and supplemental lighting was provided with overhead metal halide 1000-Watt lamps as necessary. The plants were employed for testing when they reached the second or third true leaf stage.

Treatments consisted of the benzyl ester of 4-amino-3-chloro-5-fluoro-6-(4-chloro-2-fluoro-3-methoxy-phenyl)pyridine-2-carboxylic acid (Compound A), formulated as an SC, a second cereal herbicide alone and then both in combination.

Forms of compound A (compound of formula I) tested include:

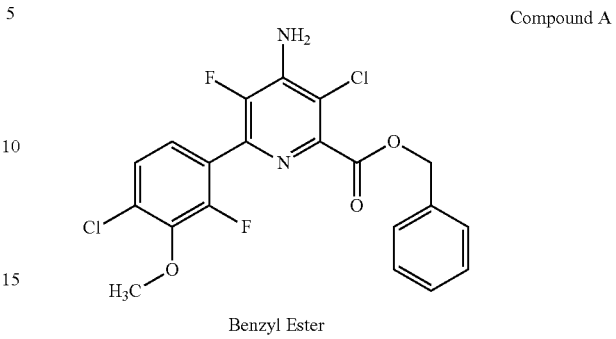

Benzyl Ester

Other herbicidal components were applied on an active ingredient basis and included acetolactate synthase (ALS)-inhibiting herbicides (sulfonamide chemical class) florasulam formulated as Derby® and pyroxsulam formulated as PowerFlex®. A measured aliquot of benzyl ester of 4-amino-3-chloro-5-fluoro-6-(4-chloro-2-fluoro-3-methoxy-phenyl)pyridine-2-carboxylic acid (Compound A) was placed in 25 milliliter (mL) glass vials and diluted in a volume of 1.25% (v/v) AgriDex® crop oil concentrated to obtain a stock solution. Compound requirements are based upon a 12 mL application volume at a rate of 187 liters per hectare (L/ha). Spray solutions of the second cereal herbicide and experimental compound mixtures were prepared by adding the stock solutions to the appropriate amount of dilution solution to form 12 mL spray solution with active ingredients in two- and three-way combinations. Formulated compounds were applied to the plant material with an overhead Mandel track sprayer equipped with an 8002E nozzle calibrated to deliver 187 L/ha over an application area of 0.503 square meters (m²) at a spray height of 18 inches (46 cm) above average plant canopy. Control plants were sprayed in the same manner with the solvent blank.

The treated plants and control plants were placed in a greenhouse as described above and watered by sub-irrigation to prevent wash-off of the test compounds. After 20-22 days, the condition of the test plants as compared with that of the control plants was determined visually and scored on a scale of 0 to 100 percent where 0 corresponds to no injury and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22.).

The following equation was used to calculate the expected activity of mixtures containing two active ingredients, A and B:

$$\text{Expected} = A + B - (A \times B/100)$$

A = observed efficacy of active ingredient A at the same concentration as used in the mixture.

B = observed efficacy of active ingredient B at the same concentration as used in the mixture.

The compounds tested, application rates employed, plant species tested, and results are given in Tables 16-18.

TABLE 16

Synergistic Activity of Foliar-Applied Compound A Benzyl Ester and Florasulam Herbicidal Compositions on Weed Control in a Cereal Cropping System.

Application Rate (gai/ha)

| Compound A Benzyl Ester | Florasulam | SASKR Obs | Exp | VERPE Obs | Exp | VIOTR Obs | Exp | MATCH Obs | Exp | CIRAR Obs | Exp |
|---|---|---|---|---|---|---|---|---|---|---|---|
| 5 | 0 | 57 | — | 37 | — | 13 | — | 13 | — | 40 | — |
| 0 | 3.75 | 30 | — | 10 | — | 65 | — | 65 | — | 40 | — |
| 5 | 3.75 | 93 | 71 | 50 | 43 | 75 | 70 | 90 | 70 | 97 | 64 |

TABLE 17

Synergistic Activity of Foliar-Applied Compound A Benzyl Ester and Florasulam Herbicidal Compositions on Weed Control in a Cereal Cropping System.

Application Rate (gai/ha)

| Compound A Benzyl Ester | Florasulam | LAMPU Obs | Exp | VERPE Obs | Exp | CIRAR Obs | Exp |
|---|---|---|---|---|---|---|---|
| 8.75 | 0.00 | 83 | — | 50 | — | 40 | — |
| 0 | 1.25 | 10 | — | 10 | — | 55 | — |
| 8.75 | 1.25 | 92 | 84 | 63 | 55 | 96 | 73 |

TABLE 18

Synergistic Activity of Foliar-Applied Compound A Benzyl Ester and Pyroxsulam Herbicidal Compositions on Weed Control in a Cereal Cropping System.

Application Rate (gai/ha)

| Compound A Benzyl Ester | Pyroxsulam | CIRAR Obs | Exp |
|---|---|---|---|
| 8.75 | 0.00 | 40 | — |
| 0 | 3.75 | 60 | — |
| 8.75 | 3.75 | 85 | 76 |

| | | |
|---|---|---|
| MATCH | *Chamomilla chamomilla* (L.) Rydb. | mayweed, scented |
| VERPE | *Veronica persica* Poir. | speedwell, bird's-eye |
| VIOTR | *Viola tricolor* (L.) | pansy, wild |
| CIRAR | *Cirsium arvense* (L.) Scop. | thistle, Canada |
| SASKR | *Salsola iberica* (L.) | thistle, Russian |
| LAMPU | *Lamium purpureum* (L.) | deadnettle, purple | g/ha = grams per hectare
Obs = observed value
Exp = expected value as calculated by Colby's equation Example IV Evaluation of Postemergence and Water-Injected Herbicidal Activity of Mixtures in the Field Multiple post-emergence field trials were conducted under field conditions in Tolima, Colombia; Thessaloniki, Greece; Ottobiano and Copiano, Italy; Greenville, Miss. and Eagle Lake, Tex., USA; and water-injected treatments were tested at Ryugasaki, Japan. Trial sites were located in commercially grown fields of direct-seeded rice (*Oryza sativa*) using standard herbicide small plot research methodology, except in Japan where transplanted rice was utilized for the field trial. Post-emergence trial plot size varied from 2 to 3 meter (m)×5 to 8 m (width×length) with 4 replicates per treatment. Water-injected trial plot size was 2×2 m with 3 replicates per treatment. The rice crop was grown using normal cultural practices for fertilization, seeding, watering, flooding and maintenance to ensure good growth of the crop and the weeds.

All treatments in the post-emergence field trials were applied using a backpack compressed air/gas sprayer with flat fan nozzles (80° or 110°) calibrated to apply 187 to 300 L/ha spray volume at approximately 200-400 kPa nozzle pressure. In Japan, treatments were water-injected applied where the specified amount of commercial product was mixed in 100 mls of water per replicate and applied directly into 3 cm deep water containing the crop and weeds. Treatments consisted of the benzyl ester of 4-amino-3-chloro-5-fluoro-6-(4-chloro-2-fluoro-3-methoxy-phenyl)pyridine-2-carboxylic acid (Compound A), formulated as an SC (suspension concentrate), and various herbicidal components alone and in combination.

Forms of compound A (compound of formula I) tested include:

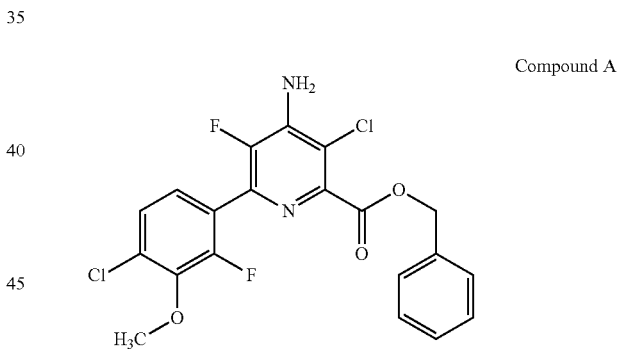

Benzyl Ester

Commercially available products of penoxsulam (Viper 20OD® (Europe), Grasp 240SC® (USA), and Wideattack 37.5SC® (Japan)) were mixed in water at appropriate formulated product rates to achieve the desired rates based on a unit area of application (hectare) to achieve the desired rates as shown. Treatments were rated at 15 to 56 days after application (DAA) as compared to the untreated control plants. Visual weed control was scored on a scale of 0 to 100 percent where 0 corresponds to no injury and 100 corresponds to complete kill.

All treatment results, both for the single product and mixtures, are an average of 3 to 4 replicates. The trial sites had naturally occurring populations of weeds. The weed spectrum included, but was not limited to, broadleaf signalgrass (*Brachiaria platyphylla* (Griseb.) Nash or *Urochloa platyphylla* (Nash) R.D. Webster, BRAPP), smallflower umbrellaplant (*Cyperus difformis* L., CYPDI), yellow nutsedge (*Cyperus*

*esculentus* L., CYPES), multiple *Echinochloa* species in the same field (ECHSS) in Italy (mixed ECHSS biotypes), Amazon sprangletop (Leptochloa panicoides (J. Presl) A.S. Hitchc., LEFPA), and Japanese bulrush (Schoenoplectus juncoides (Roxb.) Palla, SCPJU).

The compounds tested, application rates employed, plant species tested, and results from in-crop field trials are given in Tables 19-21.

TABLE 19

Synergistic Activity of Foliar-Applied Compound A Benzyl Ester and Penoxsulam Herbicidal Compositions on Weed Control in a Rice Cropping System when evaluated 15 to 19 DAA (Days After Application) in the United States.

| Compound A | | Visual Weed Control (%) - 15-19 DAA | | | |
|---|---|---|---|---|---|
| Benzyl Ester | Penoxsulam | BRAPP | | LEFPA | |
| gae/ha | gai/ha | Obs | Exp | Obs | Exp |
| 24 | 0 | — | — | 53 | — |
| 0 | 40 | — | — | 16 | — |
| 24 | 40 | — | — | 88 | 60 |
| 32 | 0 | 62 | — | — | — |
| 0 | 40 | 35 | — | — | — |
| 32 | 40 | 89 | 76 | — | — |

TABLE 20

Synergistic Activity of Foliar-Applied Compound A Benzyl Ester and Penoxsulam Herbicidal Compositions on Weed Control in a Rice Cropping System when evaluated 54-56 DAA (Days After Application) in Greece and Italy.

| Compound A Benzyl Ester | | Visual Weed Control (%) - 54-56 DAA | | | | | |
|---|---|---|---|---|---|---|---|
| Ester | Penoxsulam | CYPDI | | CYPES | | ECHSS | |
| gae/ha | gai/ha | Obs | Exp | Obs | Exp | Obs | Exp |
| 24 | 0 | 81 | — | 15 | — | 40 | — |
| 0 | 40 | 0 | — | 55 | — | 50 | — |
| 24 | 40 | 97 | 81 | 76 | 62 | 84 | 70 |

TABLE 21

Synergistic Activity of In-Water Applications of Compound A Benzyl and Penoxsulam Herbicidal Compositions on Weed Control in a Rice Cropping System when evaluated 28 DAA (Days After Application) in Japan.

| Compound A Benzyl Ester | Penoxsulam | Visual Weed Control (%) - 28 DAA SCPJU | |
|---|---|---|---|
| gae/ha | gai/ha | Obs | Exp |
| 150 | 0 | 22 | — |
| 0 | 50 | 20 | — |
| 150 | 50 | 60 | 38 |
| 200 | 0 | 25 | — |
| 0 | 50 | 20 | — |
| 200 | 50 | 68 | 42 |

BRAPP *Brachiaria platyphylla* (Griseb.) Nash or *Urochloa platyphylla* (Nash) R.D. Webster — signalgrass, broadleaf LEFPA *Leptochloa panicoides*(Presl.) Hitchc. — Amazon sprangletop
CYPDI *Cyperus difformis* L. — smallflower umbrella sedge
CYPES *Cyperus esculentus* L. — yellow nutsedge
ECHSS *Echinochloa* spp.
SCPJU *Schoenoplectus juncoides* Roxb. — Japanese bulrush
gae/ha = grams acid equivalent per hectare
gai/ha = grams active ingredient per hectare
Obs = observed value
Exp = expected value as calculated by Colby's equation
DAA = days after application

What is claimed is:

1. A herbicidal composition comprising an herbicidally effective amount of (a) a compound of the formula (I):

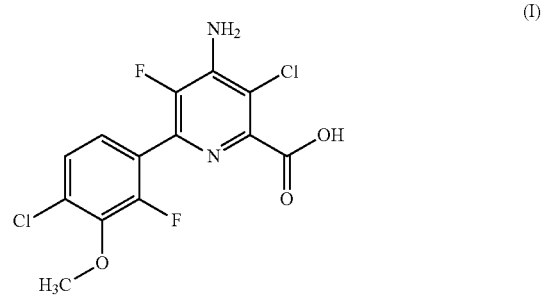 [SMILES: COc1c(Cl)ccc(-c2nc(C(=O)O)c(Cl)c(N)c2F)c1F]

a $C_1$-$C_4$ alkyl or benzyl ester, or an agriculturally acceptable salt of formula (I); and (b) a triazolopyrimidine sulfonamide herbicide or an agriculturally acceptable salt thereof, wherein the composition comprising (a) and (b) exhibits synergy.

2. The composition of claim 1, wherein (a) is a benzyl ester of formula (I).

3. The composition of claim 1, wherein (a) is the compound of formula (I), which is the carboxylic acid.

4. The composition of claim 1, wherein the (b) is cloransulam-methyl, diclosulam, florasulam, flumetsulam, metosulam, penoxsulam, or pyroxsulam or an agriculturally acceptable salt, carboxylic acid, carboxylate salt, or ester thereof.

5. The composition of claim 1, further comprising a herbicide safener, adjuvant and/or carrier.

6. The composition of claim 1, wherein the triazolopyrimidine sulfonamide is cloransulam-methyl or agriculturally acceptable salt, carboxylic acid, carboxylate salt, or ester thereof and wherein the weight ratio of compound of formula (I) or agriculturally acceptable salt or ester thereof to cloransulam-methyl or agriculturally acceptable salt, carboxylic acid, carboxylate salt, or ester thereof is from about 1:1 to about 20:1.

7. The composition of claim 1, wherein the triazolopyrimidine sulfonamide is diclosulam or agriculturally acceptable salt thereof and wherein the weight ratio of the compound of formula (I) or agriculturally acceptable salt or ester thereof to diclosulam or agriculturally acceptable salt thereof is from about 1:0.4 to about 0.7:1.

8. The composition of claim 1, wherein the triazolopyrimidine sulfonamide is florasulam or agriculturally acceptable salt thereof and wherein the weight ratio of the compound of formula (I) or agriculturally acceptable salt or ester thereof to florasulam, of agriculturally acceptable salt thereof is from about 1:0.75 to about 7:1.

9. The composition of claim 1, wherein the triazolopyrimidine sulfonamide is flumetsulam or agriculturally acceptable salt thereof and wherein the weight ratio of the compound of formula (I) or agriculturally acceptable salt or ester thereof to flumetsulam or agriculturally acceptable salt thereof is from about 1:32 to about 45:1.

10. The composition of claim 1, wherein the triazolopyrimidine sulfonamide is metosulam or agriculturally acceptable salt thereof and wherein the weight ratio of the compound of formula (I) or agriculturally acceptable salt or ester thereof to metosulam or agriculturally acceptable salt or thereof is from about 1:0.8 to about 5:1.

11. The composition of claim 1, wherein the triazolopyrimidine sulfonamide is penoxsulam or agriculturally acceptable salt thereof and wherein the weight ratio of the compound of formula (I) or agriculturally acceptable salt or ester thereof to penoxsulam or agriculturally acceptable salt thereof is from about 1:1 to about 9.6:1.

12. The composition of claim 1, wherein the triazolopyrimidine sulfonamide is pyroxsulam or agriculturally acceptable salt thereof and wherein the weight ratio of the compound of formula (I) or agriculturally acceptable salt or ester thereof to pyroxsulam or agriculturally acceptable salt thereof is from about 2:0.4 to about 3:1.

13. A method of controlling undesirable vegetation, comprising the step of:
contacting a plant, wherein the plant is undesirable vegetation or the locus thereof or applying to soil or to water, wherein the soil or the water allows the growth of the undesirable vegetation, a herbicidally effective amount of a combination comprising:
(a) a compound of the formula (I);

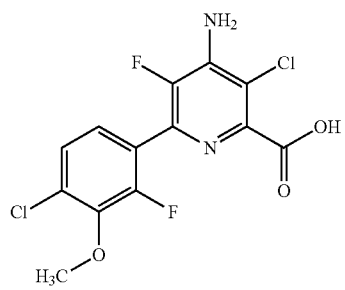

(I)

a $C_1$-$C_4$ alkyl or benzyl ester, or an agriculturally acceptable salt of formula (I); and
(b) a triazolopyrimidine sulfonamide herbicide or an agriculturally active salt thereof, wherein the combination of (a) and (b) exhibits synergy for the control of undesirable vegetation, wherein the undesirable vegetation effects a desirable direct seeded plant, or a water seeded plant, or a transplanted plant selected from the group consisting of: rice, cereals, wheat, barley, oats, rye, sorghum, and corn/maize.

14. The method of claim 13, wherein the water is part of a flooded rice paddy.

15. The method of claim 13, wherein the undesirable vegetation is selected from the group consisting of glyphosate-, 5-enolpyruvylshikimate-3-phosphate (EPSP) synthase inhibitor-, glufosinate-, glutamine synthetase inhibitor-, dicamba-, phenoxy auxin-, pyridyloxy auxin-, synthetic auxin-, auxin transport inhibitor-, aryloxyphenoxypropionate-, cyclohexanedione-, phenylpyrazoline-, acetyl CoA carboxylase (ACCase) inhibitor-, imidazolinone-, sulfonylurea-, pyrimidinylthiobenzoate-, triazolopyrimidine-, sulfonylaminocarbonyltriazolinone-, acetolactate synthase (ALS) or acetohydroxy acid synthase (AHAS) inhibitor-, 4-hydroxyphenyl-pyruvate dioxygenase (HPPD) inhibitor-, phytoene desaturase inhibitor-, carotenoid biosynthesis inhibitor-, protoporphyrinogen oxidase (PPO) inhibitor-, cellulose biosynthesis inhibitor-, mitosis inhibitor-, microtubule inhibitor-, very long chain fatty acid inhibitor-, fatty acid and lipid biosynthesis inhibitor-, photosystem I inhibitor-, photosystem II inhibitor-, protoporphyrinogen oxidase (PPO) inhibitor-, triazine-, or bromoxynil-tolerant crops.

16. The method of claim 13, wherein the desirable plant possesses multiple or stacked traits conferring tolerance to multiple herbicides.

17. The method of claim 13, wherein the undesirable vegetation comprises a herbicide resistant or tolerant weed.

18. The method of claim 17, wherein the resistant or tolerant weed is a biotype resistant or tolerant to acetolactate synthase (ALS) inhibitors or acetohydroxy acid synthase (AHAS), photosystem II inhibitors, acetyl CoA carboxylase (ACCase) inhibitors, synthetic auxins, auxin transport inhibitors, photosystem I inhibitors, 5-enolpyruvylshikimate-3-phosphate (EPSP) synthase inhibitors, microtubule assembly inhibitors, fatty acid and lipid synthesis inhibitors, protoporphyrinogen oxidase (PPO) inhibitors, carotenoid biosynthesis inhibitors, very long chain fatty acid (VLCFA) inhibitors, phytoene desaturase (PDS) inhibitors, glutamine synthetase inhibitors, 4-hydroxyphenyl-pyruvate-dioxygenase (HPPD) inhibitors, mitosis inhibitors, cellulose biosynthesis inhibitors, herbicides with multiple modes-of-action, quinclorac, arylaminopropionic acids, difenzoquat, endothall, or organoarsenicals.

* * * * *

UNITED STATES PATENT AND TRADEMARK OFFICE
CERTIFICATE OF CORRECTION

| | | |
|---|---|---|
| PATENT NO. | : 8,906,825 B2 | Page 1 of 3 |
| APPLICATION NO. | : 13/832978 | |
| DATED | : December 9, 2014 | |
| INVENTOR(S) | : Richard K. Mann | |

It is certified that error appears in the above-identified patent and that said Letters Patent is hereby corrected as shown below:

In the Claims

Column 46, line 15-37, claim 1 should read

1. A herbicidal composition comprising an herbicidally effective amount of (a) a compound of the formula (I):

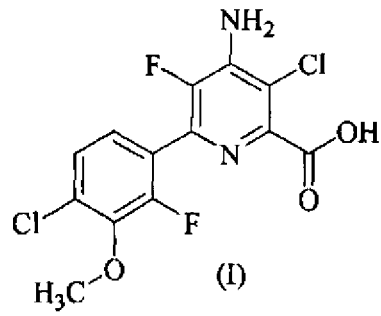

or a $C_1$-$C_4$ alkyl or benzyl ester, or an agriculturally acceptable salt of formula (I); and (b) a triazolopyrimidine sulfonamide herbicide or an agriculturally acceptable salt thereof, wherein the (a) and (b) are present in the composition in a ratio such that the composition_exhibits synergy.

Column 47, line 25 to Column 48, line 6, claim 13 should read

13. A method of controlling undesirable vegetation, comprising the step of:

contacting a plant, wherein the plant is undesirable vegetation or the locus thereof,_or applying to soil or to water, wherein the soil or the water allows the growth of the undesirable vegetation, a Signed and Sealed this
Twenty-first Day of April, 2015

Michelle K. Lee
*Director of the United States Patent and Trademark Office* herbicidally effective amount of a combination comprising:

(a) a compound of the formula (I):

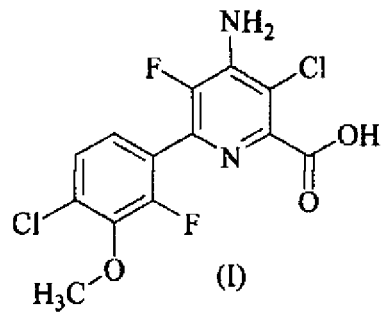

or a $C_1$-$C_4$ alkyl or benzyl ester, or an agriculturally acceptable salt of formula (I); and (b) a triazolopyrimidine sulfonamide herbicide or an agriculturally active salt thereof, wherein (a) and (b) are present in the combination in a ratio such that the combination_exhibits synergy for the control of undesirable vegetation, wherein the undesirable vegetation effects a desirable direct seeded plant, or a water seeded plant, or a transplanted plant selected from the group consisting of: rice, cereals, wheat, barley, oats, rye, sorghum, and corn/maize.

Column 48, lines 9-28, claim 15 should read

15. The method of claim 13, wherein the undesirable vegetation is selected from the group consisting of glyphosate-, 5-enolpyruvylshikimate-3-phosphate synthase inhibitor-, glufosinate-, glutamine synthetase inhibitor-, dicamba-, phenoxy auxin-, pyridyloxy auxin-, synthetic auxin-, auxin transport inhibitor-, aryloxyphenoxypropionate-, cyclohexanedione-, phenylpyrazoline-, acetyl CoA carboxylase inhibitor-, imidazolinone-, sulfonylurea-, pyrimidinylthiobenzoate-, triazolopyrimidine-, sulfonylaminocarbonyltriazolinone-, acetolactate synthase or acetohydroxy acid synthase inhibitor-, 4-hydroxyphenyl-pyruvate dioxygenase inhibitor-, phytoene desaturase inhibitor-, carotenoid biosynthesis inhibitor-, protoporphyrinogen oxidase inhibitor-, cellulose biosynthesis inhibitor-, mitosis inhibitor-, microtubule inhibitor-, very long chain fatty acid inhibitor-, fatty acid and lipid biosynthesis inhibitor-, photosystem I inhibitor-, photosystem II inhibitor-, protoporphyrinogen oxidase inhibitor-, triazine-, or bromoxynil-tolerant crops.

Column 48, lines 29-31, claim 16 should read

16. The method of claim 13, wherein the tolerant crop possesses multiple or stacked traits conferring tolerance to multiple herbicides.

CERTIFICATE OF CORRECTION (continued)
U.S. Pat. No. 8,906,825 B2

Column 48, Line 32-33, claim 17 should read

17. The method of claim 13, wherein the undesirable vegetation comprises a herbicide resistant or tolerant plant.

Column 48, lines 34-49, claim 18 should read

18. The method of claim 17, wherein the resistant or tolerant plant is resistant or tolerant to acetolactate synthase inhibitors or acetohydroxy acid synthase, photosystem II inhibitors, acetyl CoA carboxylase inhibitors, synthetic auxins, auxin transport inhibitors, photosystem I inhibitors, 5-enolpyruvylshikimate-3-phosphate synthase inhibitors, microtubule assembly inhibitors, fatty acid and lipid synthesis inhibitors, protoporphyrinogen oxidase inhibitors, carotenoid biosynthesis inhibitors, long chain fatty acid inhibitors, phytoene desaturase inhibitors, glutamine synthetase inhibitors, 4-hydroxyphenyl-pyruvate-dioxygenase inhibitors, mitosis inhibitors, cellulose biosynthesis inhibitors, herbicides with multiple modes-of-action, quinclorac, arylaminopropionic acids, difenzoquat, endothall, or organoarsenicals.